(12) United States Patent
Kuttruff et al.

(10) Patent No.: US 12,391,667 B2
(45) Date of Patent: Aug. 19, 2025

(54) N-METHYL, N-(6-(METHOXY)PYRIDAZIN-3-YL) AMINE DERIVATIVES AS AUTOTAXIN (ATX) MODULATORS FOR THE TREATMENT OF INFLAMMATORY AIRWAY OR FIBROTIC DISEASES

(71) Applicant: Boehringer Ingelheim International GmbH, Ingelheim am Rhein (DE)

(72) Inventors: Christian Andreas Kuttruff, Schemmerhofen (DE); Cedrickx Godbout, Attenweiler (DE); Hannes Fiepko Koolman, Biberach (DE); Gerald Juergen Roth, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 742 days.

(21) Appl. No.: 17/629,024

(22) PCT Filed: Jul. 21, 2020

(86) PCT No.: PCT/EP2020/070553
§ 371 (c)(1),
(2) Date: Jan. 21, 2022

(87) PCT Pub. No.: WO2021/013833
PCT Pub. Date: Jan. 28, 2021

(65) Prior Publication Data
US 2022/0281838 A1    Sep. 8, 2022

(30) Foreign Application Priority Data
Jul. 22, 2019 (EP) ..................... 19187616

(51) Int. Cl.
C07D 401/12 (2006.01)
C07D 401/14 (2006.01)

(52) U.S. Cl.
CPC .......... *C07D 401/12* (2013.01); *C07D 401/14* (2013.01)

(58) Field of Classification Search
None
See application file for complete search history.

(56) References Cited

U.S. PATENT DOCUMENTS

| | | | |
|---|---|---|---|
| 11,104,665 B2* | 8/2021 | Roth | A61P 29/00 |
| 11,485,727 B2 | 11/2022 | Kuttruff et al. | |
| 2009/0143385 A1 | 6/2009 | Buettelmann et al. | |
| 2010/0197908 A1* | 8/2010 | Lehmann-Lintz | A61P 25/24 |
| | | | 544/114 |
| 2016/0168119 A1 | 6/2016 | Baettig et al. | |
| 2016/0287584 A1 | 10/2016 | Gibson et al. | |
| 2018/0127425 A1 | 5/2018 | Desroy et al. | |
| 2018/0282311 A9 | 10/2018 | Hadida Ruah et al. | |
| 2020/0131151 A1 | 4/2020 | Roth et al. | |
| 2021/0024492 A1 | 1/2021 | Kuttruff et al. | |
| 2021/0024495 A1 | 1/2021 | Kuttruff et al. | |
| 2022/0298118 A1 | 9/2022 | Takahashi et al. | |

FOREIGN PATENT DOCUMENTS

| | | |
|---|---|---|
| WO | 2007022937 A1 | 3/2007 |
| WO | 2011133882 A1 | 10/2011 |
| WO | 2012166415 A1 | 12/2012 |
| WO | 2013061297 A1 | 5/2013 |
| WO | 2014097151 A2 | 6/2014 |
| WO | 2014139882 A1 | 9/2014 |
| WO | 2014179144 A1 | 11/2014 |
| WO | 2014202458 A1 | 12/2014 |
| WO | 2017050747 A1 | 3/2017 |
| WO | 2017148787 A1 | 9/2017 |
| WO | 2018212534 A1 | 11/2018 |
| WO | 2020089098 A1 | 5/2020 |
| WO | 2021013830 A1 | 1/2021 |
| WO | 2021013832 A1 | 1/2021 |
| WO | 2021013833 A1 | 1/2021 |
| WO | 2021014365 A1 | 1/2021 |
| WO | 2021014386 A1 | 1/2021 |

OTHER PUBLICATIONS

Kihara et al. Exp Cell Res. May 1, 2015; 333(2): 171-177. (Year: 2015).*
Zulfikar et al. Clinical Pharmacology: Advances and Applications 2020: 12 97-108. (Year: 2020).*
Kuttruff et al., "Discovery of BI-2545: A Novel Autotaxin Inhibitor That Significantly Reduces LPA Levels in Vivo", ACS Medicinal Chemistry Letters, 2017, 8, pp. 1252-1257.
International Search Report and Written Opinion for corresponding application, PCT/EP2020/070553, Date of mailing Aug. 26, 2020.
Bretschneider, Tom et al. "Ultrafast and Predictive Mass Spectrometry-Based Autotaxin Assays for Label-Free Potency Screening", (2017) SLAS Discovery, vol. 22(4), 425-432.
Budd, David C. et al. "Development of lysophosphatidic acid pathway modulators as therapies for fibrosis" (2013) Future Medicinal Chemistry, vol. 5, Issue 16, 1935-1952.

(Continued)

*Primary Examiner* — Adam C Milligan
*Assistant Examiner* — Jed A Kucharczk
(74) *Attorney, Agent, or Firm* — Philip I. Datlow

(57) ABSTRACT

The present invention relates to N-methyl, N-(6-(methoxy) pyridazin-3-yl) amine derivatives as autotaxin (ATX) modulators for the treatment of inflammatory airway or fibrotic diseases such as e.g. idiopathic lung disease (IFF) or systemic sclerosis (SSc). The present description discloses the preparation of exemplary compounds (e.g. pages 37 to 45; examples 1.1 to 1.13) as well as relevant biological data thereof (e.g. pages 12 to 17, tables 1 to 9). An exemplary compound is e.g. 1-[4-(4-{1-[(6-{[6-(trifluoromethyl) pyridin-3-yl]methoxy}pyridazin-3-yl)amino]cyclopropyl}-phenyl) piperazin-1-yl]ethan-1-one (example 1.1).

3 Claims, No Drawings

(56) References Cited

OTHER PUBLICATIONS

Castagna, Diana et al. "Development of Autotaxin Inhibitors: An Overview of the Patent and Primary Literature" (2016) Journal of Medicinal Chemistry, 59, 5604-5621.
Castelino, Flavia V. et al. "An Autotaxin-LPA-IL-6 Amplification Loop Drives Scleroderma Fibrosis", (2016) Arthritis Rheumatol., vol. 68, Issue 12, 2964-2974.
Denton, Christopher P et al. "Systemic sclerosis", (2017) Lancet, vol. 390, 1685-1699.
Desroy, Nicholas et al. "Discovery of 2-[[2-Ethyl-6-[4-[2-(3-hydroxyazetidin-1-yl)-2-oxoethyl]piperazin-1-yl]-8-methylimidazo[1,2-a]pyridin-3-yl]methylamino]-4-(4-fluoropheynyl)thiazole-5-carbonitrile (GLPG1690), a First-in-Class Autotaxin Inhibitor Undergoing Clinical Evaluation for the Treatment of Idiopathic Pulmonary Fibrosis" (2017) Journal of Medicinal Chemistry, 60: 3580-3590.
Du Bois, R.M. "Strategies for treating idiopathic pulmonary fibrosis", (2010) Nature Reviews Drug Discovery, vol. 9, 129-140.
Dyson et al., Chemistry of Synthetic Medicinal Substances, 1964, pp. 12-19.
Guiducci, Serena et al. "A New Way of Thinking about Systemic Sclerosis: The Opportunity for a Very Early Diagnosis", (2016) Israel Medical Association Journal, vol. 18, 141-143.
Houben, Anna J.S. et al. "Autotaxin and LPA Receptor Signaling in Cancer" (2011) Cancer Metastasis Rev, 30: 557-565.
Kihara, Yasuyuki et al. "Lysophospholipid receptors in drug discovery" (2016) Exp Cell Res., 333(2):171-177.
Kuttruff et al., "Discovery of BI-2545: A Novel Autotaxin Inhibitor that Significantly Reduces LPA Levels in Vivo" (2017) ACS Medicinal Chemistry Letters, 8, pp. 1252-1257.
Leroy, EC et al. "Scleroderma (systemic sclerosis): classification, subsets and pathogenesis" The Journale of Rheumatology, (1988), vol. 15, Issue 2, 202-205.
Montesi, Sydney B. et al. "Docosatetraenoyl LPA is elevated in exhaled breath condensate in idiopathic pulmonary fibrosis" (2014), BMC Pulmonary Medicine, vol. 14, Issue 1, 1-7.
NIH—National Heart, Lung, and Blood Institute, Idiopathic Pulmonary Fibrosis Treatment. Retrieved from the internet on Dec. 27, 2022, https ://www .nhlbi .nih .gov/health/idiopathic-pulmonary-fl brosis/treatment.
Oikonomou, Nikos et al. "Pulmonary autotaxin expression contributes to the pathogenesis of pulmonary fibrosis", (2012) American Journal Respiratory Cell Molecular Biology, vol. 47, Issue 5, 566-574.
Pokrovskij, V.I., Popular Medical Encyclopedia, 4th edition, 1997, p. 317.
Raghu, Ganesh et al. "An Official ATS/ERS/JRS/ALAT Statement: Idiopathic Pulmonary Fibrosis: Evidence-based Guidelines for Diagnosis and Management", (2011) American Journal of Respiratory and Critical Care Medicine, vol. 183, 788-824.
Rindlisbacher, Barbara et al. "Serum metabolic profiling identified a distinct metabolic signature in patients with idiopathic pulmonary fibrosis—a potential biomarker role for LysoPC", (2018), Respiratory Research, vol. 19, Issue 1, 1-12.
Rongioletti, F et al. "Scleredema. A multicentre study of characteristics, comorbidities, course and therapy in 44 patients", (2015) Journal of the European Academy of Dermatology and Venereology, vol. 29, 2399-2404.
Scherer, Max et al. "High-Throughput Analysis of Sphingosine 1-Phosphate, Sphinganine 1-Phosphate, and Lysophosphatidic Acid in Plasma Samples by Liquid Chromatography-Tandem Mass Spectrometry", (2009) Clinical Chemistry, vol. 55, 1218-1222.
Swaney, JS et al. "A novel, orally active LPA1 receptor antagonist inhibits lung fibrosis in the mouse bleomycin model" (2010) British Journal of Pharmacology, vol. 160, Issue 7, 1699-1713.
Tager, Andrew M. et al. "The lysophosphatidic acid receptor LPA1 links pulmonary fibrosis to lung injury by mediating fibroblast recruitment and vascular leak", (2008) Nature Medicine,vol. 14, Issue 1, 45-54.
Tyndall, Anthony et al. "Causes and risk factors for death in systemic sclerosis: a study from the EULAR Scleroderma Trials and Research (EUSTAR) database", (2010) Annals of the Rheumatic Diseases, vol. 69, 1809-1815.
Zulfikar, Sabrina et al. "Inhibitors of the Autotaxin-Lysophosphatidic Acid Axis and Their Potential in the Treatment of Interstitial Lung Disease: Current Perspectives" (2020) Clinical Pharmacology: Advances and Applications: 12, 97-108.

\* cited by examiner

N-METHYL, N-(6-(METHOXY)PYRIDAZIN-3-YL) AMINE DERIVATIVES AS AUTOTAXIN (ATX) MODULATORS FOR THE TREATMENT OF INFLAMMATORY AIRWAY OR FIBROTIC DISEASES

FIELD OF THE INVENTION

The present invention relates to novel pyridazines, processes for their preparation, pharmaceutical compositions containing them and their use in therapy, particularly in the treatment and/or prevention of diseases and disorders mediated by Autotaxin.

BACKGROUND OF THE INVENTION

Autotaxin (ATX; ENPP2) is a secreted enzyme responsible for hydrolysing lysophosphatidylcholine (LPC) to the bioactive lipid lysophosphatidic acid (LPA) through its lysophospholipase D activity. In turn, LPA exerts its effects by interacting with six GPCRs (LPA Receptors 1-6, LPAR1-6) (Houben A J, 2011). ATX-LPA signalling has been implicated for example in angiogenesis, chronic inflammation, autoimmune diseases, fibrotic diseases, cancer progression and tumor metastasis. For example, LPA, acting on LPAR1, induces lung fibroblast migration, proliferation and differentiation; modulates epithelial and endothelial barrier function; and promotes lung epithelial cell apoptosis (Budd, 2013). ATX inhibition, LPAR1 gene deletion and selective LPAR1 antagonists have been shown to be effective in pre-clinical models of fibrosis of the lung and skin (Tager A M, 2008; Swaney J, 2010, Casetelino F V, 2016).

In Idiopathic Pulmonary Fibrosis (IPF) patients, LPA levels in bronchoalveolar lavage fluid are increased (Tager et al., 2008, Nat. Med.) and increased concentrations of ATX were detected in human fibrotic lung tissue. (Oikonomou et al., 2012, AJRCMB). LPA levels are elevated in the exhaled breath condensate of IPF subjects (Montesi et al., 2014_BMCPM), and LPC is increased 2-fold in serum of stable IPF patients (Rindlisbacher et al., 2018, Resp. Res.).

Therefore, increased ATX levels and/or increased levels of LPA, altered LPA receptor expression, and altered responses to LPA may affect a number of pathophysiological conditions related to ATX-LPA signaling.

Interstitial Lung Diseases (ILDs) are characterized by inflammation and fibrosis of the interstitium, the tissue and space between the air sacs of the lung (du Bois, Nat. Rev. Drug Discov. 2010, 9, 129-140). An ILD may occur when an injury to the lungs triggers an abnormal healing response. ILDs thus also include Progressive Fibrosing Interstitial Lung Diseases (PFILDs) wherein the response to lung injury becomes progressive, self-sustaining and independent of the original clinical association or trigger. The most prominent PFILDs are Idiopathic Pulmonary Fibrosis (IPF) and Systemic Sclerosis-ILD (SSc-ILD). IPF is a chronic fibrotic irreversible and ultimately fatal lung disease characterized by a progressive fibrosis in the interstitium in the lung, leading to a decreasing lung volume and progressive pulmonary insufficiency. IPF is also characterized by a specific histopathologic pattern known as usual interstitial pneumonia (UIP) (Raghu et al, Am. J. Respir. Crit. Care Med. 183: 788-824.).

Systemic Sclerosis (SSc) also called scleroderma is an immune-mediated rheumatic disease of complex aetiology. It is a multi-organ, heterogenic disease characterized by extensive fibrosis, vasculopathy and autoantibodies against various cellular antigens with high mortality. It is a rare disorder, an orphan disease with high unmet medical need. The early clinical signs of SSc can be varied. Raynaud's phenomenon and gastro-oesophageal reflux are often present early in the disease (Rongioletti F, et al., J Eur Acad Dermatol Venereol 2015; 29: 2399-404). Some patients present with inflammatory skin disease, puffy and swollen fingers, musculoskeletal inflammation, or constitutional manifestations such as fatigue. Excess collagen deposition in the skin of patients makes the skin thick and tough. In some patients, organ-based manifestations of the disease, like lung fibrosis, pulmonary arterial hypertension, renal failure or gastrointestinal complication is observed. In addition, one of the most common manifestations of immune involvement is the presence of abnormal levels of autoimmune antibodies to the nucleus of one's own cells (antinuclear antibodies or ANA) that are seen in nearly everyone with SSc (Guiducci S et al., Isr Med Assoc J 2016; 18: 141-43). ILD and pulmonary arterial hypertension (PAH) are the most frequent causes of death in patients of SSc (Tyndall A J et al. Ann Rheum Dis 2010; 69: 1809-15).

SSc patients are classified into two major disease subsets: diffuse cutaneous systemic sclerosis, and limited cutaneous systemic sclerosis (LeRoy E C, et al., J Rheumatol 1988; 15:202-5). Three clinical features—excessive fibrosis (scarring), vasculopathy, and autoimmunity—appear to underlie the processes that result in the different manifestations that characterize SSc. SSc is currently considered as a manifestation of dysregulated or dysfunctional repair of connective tissue to injury (Denton C P et al., Lancet 2017; 390: 1685-99).

It is therefore desirable to provide potent ATX inhibitors.

ATX inhibitors of various structural classes are reviewed in D. Castagna et al. (J. Med. Chem. 2016, 59, 5604-5621). WO2014/139882 discloses compounds that are inhibitors of ATX, having the generalized structural formula

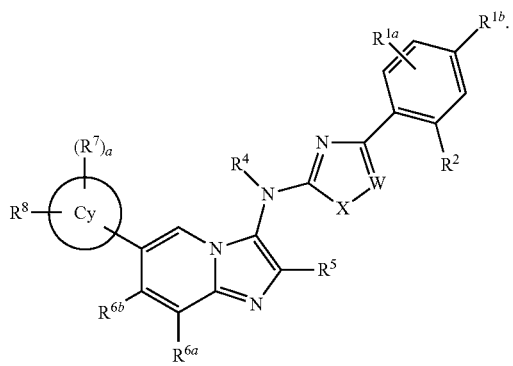

Example 2 therein is further disclosed in N. Desroy, et al (J. Med. Chem. 2017, 60, 3580-3590 as example 11) as a first-in-class ATX inhibitor undergoing clinical evaluation for the treatment of idiopathic pulmonary fibrosis. In C. Kuttruff, et al. (ACS Med. Chem. Lett. 2017, 8, 1252-1257) ATX inhibitor BI-2545 (example 19) is disclosed that significantly reduces LPA levels in vivo.

DETAILED DESCRIPTION OF THE INVENTION

The present invention provides novel pyridazines that are surprisingly potent inhibitors of autotaxin (Assay A), further characterized by
high potency in human whole blood (Assay B), and
significant reduction in the plasma concentration levels of LPA in vivo over several hours (Assay C).

Compounds of the present invention are useful as agents for the treatment or prevention of diseases or conditions in which ATX activity and/or LPA signalling participates, is involved in the etiology or pathology of the disease, or is otherwise associated with at least one symptom of the disease. ATX-LPA signalling has been implicated for example in angiogenesis, chronic inflammation, autoimmune diseases, fibrotic diseases, cancer progression and tumor metastasis.

Compounds of the invention are superior to those disclosed in the prior art in terms of the combination of the following parameters:
potency as inhibitors of ATX,
potency as inhibitors of ATX in human whole blood,
reducing the plasma concentration levels of LPA in vivo over several hours ATX is a soluble plasma protein, which is active in heparinized whole blood. Its substrate LPC is highly abundant, its concentration being in the µM range. Therefore, a whole blood assay at physiological substrate concentrations is a highly relevant assay, predictive for the efficacy of ATX inhibitors in vivo.

LPA reduction in vivo is determined by measuring the plasma concentration of LPA after oral dosage of the compounds of the present invention. LPA is a very strong bioactive lipid, which efficiently activates downstream pathways via the LPA-receptors 1-6 in a concentration dependent manner. The pronounced and sustained blockage of the LPA formation via ATX inhibition is assessed by measuring the extent of LPA reduction 8 hours after compound dosage. A high reduction of plasma LPA at 8 h is therefore highly indicative for efficacy and sustained duration of action in vivo as well as sustained target engagement of the LPA receptors.

Compounds of the present invention differ structurally from examples 2 and 12 in WO2014/139882 and example 19 in ACS Med. Chem. Lett. 2017, 8, 1252-1257, in that they contain a central pyridazine core with substituents in the 3- and 6-positions. This structural difference unexpectedly leads to a superior combination of (i) inhibition of ATX, (ii) inhibition of ATX in human whole blood, and (iii) reduced plasma concentration levels of LPA in vivo over several hours.

Consequently, compounds of the present invention demonstrate high in vivo target engagement and can be expected to have higher efficacy in humans.

The present invention provides novel compounds according to formula (I)

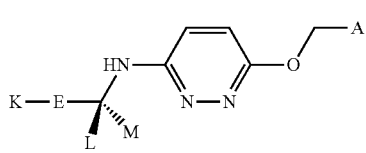

(I)

wherein
A is pyridyl substituted with one or two members of the group consisting of fluoro and $F_{1-7}$-fluoro-$C_{1-3}$-alkyl;
E is selected from the group consisting of phenyl and pyridyl optionally substituted with one or two members of the group consisting of fluoro and $C_{1-3}$-alkyl;
K is selected from the group consisting of

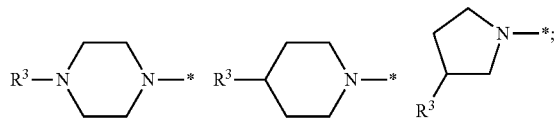

$R^3$ is selected from the group consisting of $R^4(O)C$— and $R^5(O)C(CH_3)N$—;
$R^4$ is methyl;
$R^5$ is methyl;
L and M are independently selected from the group consisting of
H, methyl and $HOH_2C$—,
or L and M form together with the carbon to which they are joined, a cyclopropyl ring.

Another embodiment of the present invention relates to a compound of formula (I), wherein A is pyridyl substituted with one or two of $F_{1-3}$-fluoro-$C_1$-alkyl; and substituents E, K, L and M are defined as in the preceding embodiment.

Another embodiment of the present invention relates to a compound of formula (I), wherein A is pyridyl substituted with one or two members of the group consisting of $F_2HC$ and $F_3C$; and substituents E, K, L and M are defined as in the preceding embodiment.

Another embodiment of the present invention relates to a compound of formula (I), wherein A is selected from the group consisting of

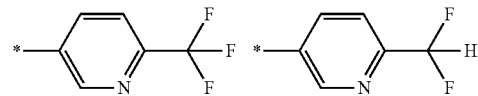

and substituents E, K, L and M are defined as in any of the preceding embodiments.

Another embodiment of the present invention relates to a compound of formula (I), wherein E is selected from the group consisting of phenyl and pyridyl optionally substituted with one or two members of the group consisting of fluoro and methyl; and substituents A, K, L and M are defined as in any of the preceding embodiments.

Another embodiment of the present invention relates to a compound of formula (I), wherein E is selected from the group consisting of

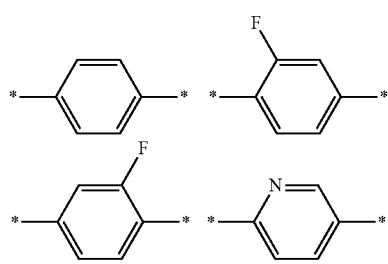

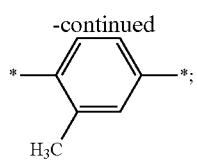
and substituents A, K, L and M are defined as in any of the preceding embodiments.
Preferred is a compound of formula (I), according to the present invention, selected from the group consisting of
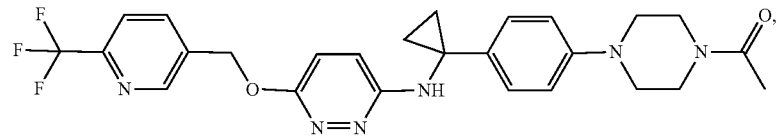
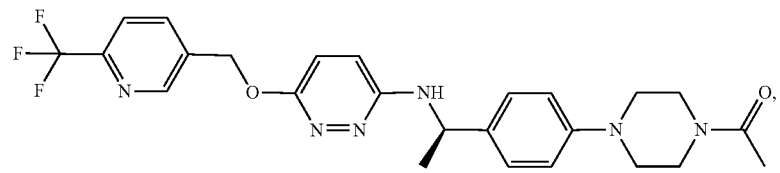
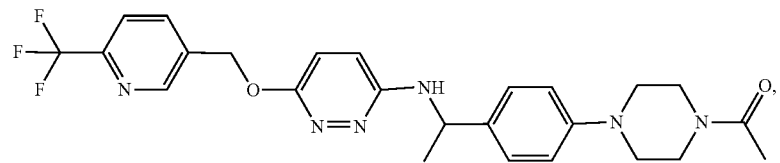
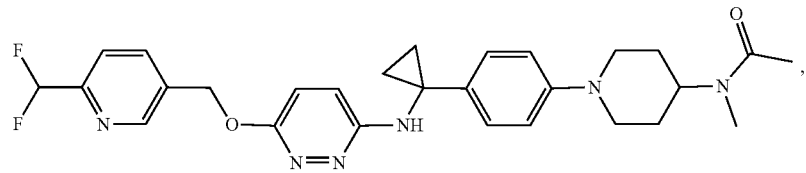
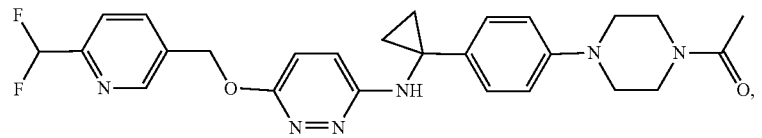
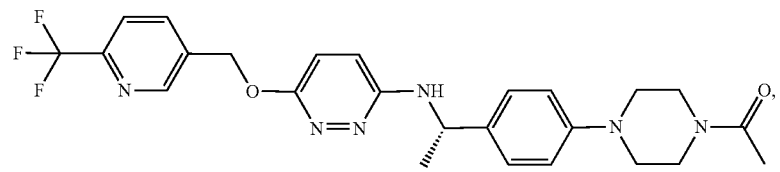
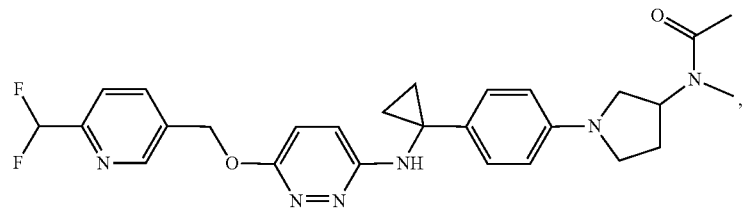
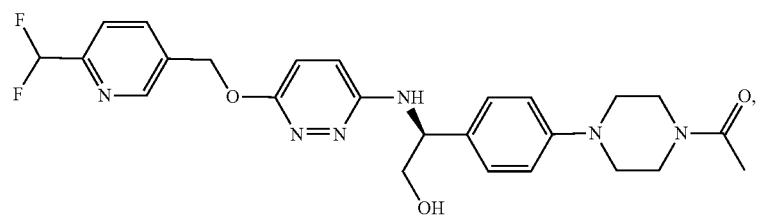

-continued

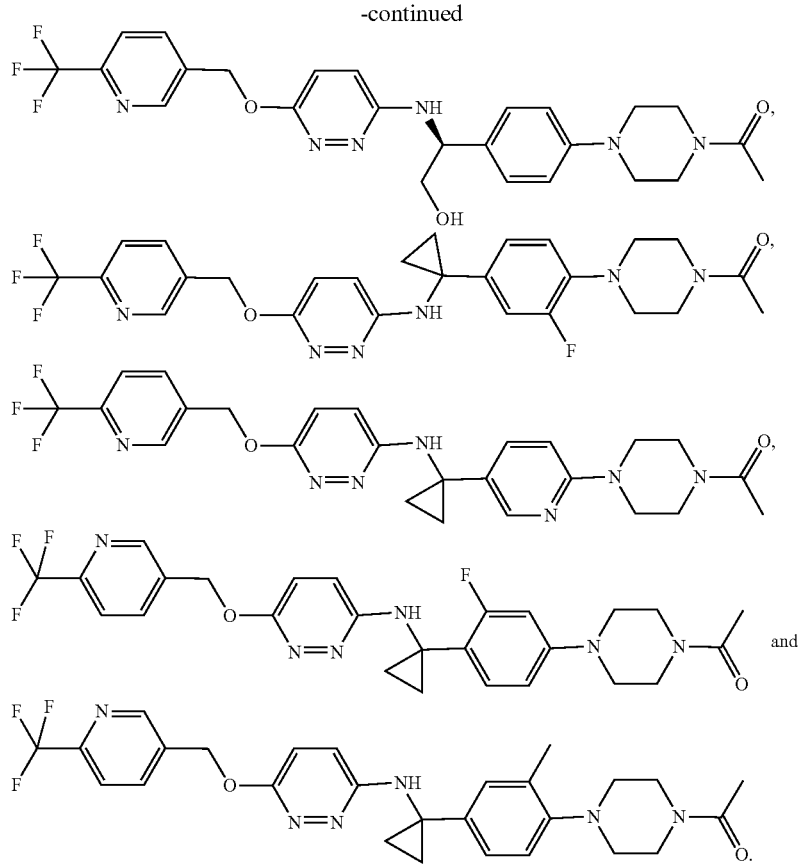

A further embodiment relates to a pharmaceutical composition comprising at least one compound of formula I according to the present invention or a pharmaceutically acceptable salt thereof and one or more pharmaceutically acceptable excipients.

A further embodiment relates to a compound of formula (I) according to the present invention, for use as a medicament.

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general in groups like HO, $H_2N$, (O)S, (O)$_2$S, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl" means an aryl group which is bound to a $C_{1-3}$-alkyl-group, the latter of which is bound to the core or to the group to which the substituent is attached. In case a compound of the present invention is depicted in form of a chemical name and as a formula in case of any discrepancy the formula shall prevail. An asterisk is may be used in sub-formulas to indicate the bond which is connected to the core molecule as defined. The numeration of the atoms of a substituent starts with the atom which is closest to the core or to the group to which the substituent is attached.

For example, the term "3-carboxypropyl-group" represents the following substituent:

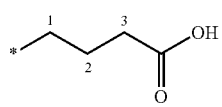

wherein the carboxy group is attached to the third carbon atom of the propyl group. The terms "1-methylpropyl-", "2,2-dimethylpropyl-" or "cyclopropylmethyl-" group represent the following groups:

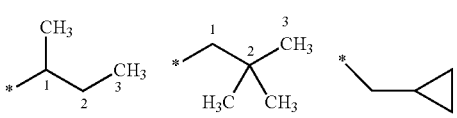

The asterisk may be used in sub-formulas to indicate the bond which is connected to the core molecule as defined.

The term "substituted" as used herein, means that any one or more hydrogens on the designated atom is replaced with a selection from the indicated group, provided that the designated atom's normal valence is not exceeded, and that the substitution results in a stable compound.

The term "$C_{1-n}$-alkyl", wherein n is an integer selected from 2, 3, 4, 5 or 6, preferably 4 or 6, either alone or in combination with another radical denotes an acyclic, saturated, branched or linear hydrocarbon radical with 1 to n C atoms. For example the term $C_{1-5}$-alkyl embraces the radicals H₃C—, H₃C—CH₂—, H₃C—CH₂—CH₂—, H₃C—CH(CH₃)—, H₃C—CH₂—CH₂—CH₂—, H₃C—CH₂—CH(CH₃)—, H₃C—CH(CH₃)—CH₂—, H₃C—C(CH₃)₂—, H₃C—CH₂—CH₂—CH₂—CH₂—, H₃C—CH₂—CH₂—CH(CH₃)—, H₃C—CH₂—CH(CH₃)—CH₂—, H₃C—CH(CH₃)—CH₂—CH₂—, H₃C—CH₂—C(CH₃)₂—, H₃C—C(CH₃)₂—CH₂—, H₃C—CH(CH₃)—CH(CH₃)— and H₃C—CH₂—CH(CH₂CH₃)—.

The term "halogen" denotes chlorine, bromine, iodine, and fluorine. By the term "halo" added to an "alkyl", "alkylene" or "cycloalkyl" group (saturated or unsaturated) is such a alkyl or cycloalkyl group wherein one or more hydrogen atoms are replaced by a halogen atom selected from among fluorine, chlorine or bromine, preferably fluorine and chlorine, particularly preferred is fluorine. Examples include: H₂FC—, HF₂C—, F₃C—.

The term phenyl refers to the radical of the following ring

The term pyridinyl refers to the radical of the following ring

The term pyridazine refers to the following ring

The term cyclopropyl refers to the following ring

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of the present invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The phrase "pharmaceutically acceptable" is employed herein to refer to those compounds, materials, compositions, and/or dosage forms which are, within the scope of sound medical judgment, suitable for use without excessive toxicity, irritation, allergic response, or other problem or complication, and commensurate with a reasonable benefit/risk ratio.

As used herein, "pharmaceutically acceptable salt" refers to derivatives of the disclosed compounds wherein the parent compound forms a salt or a complex with an acid or a base. Examples of acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Examples for cations and bases forming a pharmaceutically acceptable salt with a parent compound containing an acidic moiety include Na⁺, K⁺, Ca²⁺, Mg²⁺, NH₄⁺, L-arginine, 2,2'-iminobisethanol, L-lysine, N-methyl-D-glucamine or tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetate salts,) also comprise a part of the present invention.

Biological Assays

The biological activity of compounds was determined by the following methods:

Assay A: Biochemical ATX Assay 5 nM recombinant ATX (Cayman Chemicals) was supplemented to 50 mM Tris buffer (pH 8.0) containing 3 mM KCl, 1 mM $CaCl_2$), 1 mM $MgCl_2$ 0.14 mM NaCl, and 0.1% bovine serum albumin. Test compounds were dissolved in DMSO and tested in the range of 0.1 nM to 10 µM. The enzymatic reaction (22.5 µL) was started by addition of 2.5 µL 10 µM 18:1 LPC (Avanti Lipids, Alabaster, AL, USA). After 2-h incubation at room temperature, the reaction was stopped by addition of 20 µL water containing 500 nM 20:4 LPA as internal standard and 100 µL 1-butanol for extracting LPA. Subsequently, the plates were centrifuged at 4000 rpm, 4° C., for 2 min. The resultant upper butanol phase was directly used for injection at a RapidFire system (Agilent).

The RapidFire autosampler was coupled to a binary pump (Agilent 1290) and a Triple Quad 6500 (ABSciex, Toronto, Canada). This system was equipped with a 10-µL loop, 5-µL Waters Atlantis HILIC cartridge (Waters, Elstree, UK), 90% acetonitrile containing 10 mM ammonium acetate as eluent A and 40% acetonitrile containing 10 mM ammoniumacetate as eluent B. For details see (Bretschneider et al., SLAS Discovery, 2017). 1 The MS was operated in negative mode with a source temperature of 550° C., curtain gas=35, gas 1=65, and gas 2=80. The following transitions and MS parameters (DP: declustering potential and CE: collision energy) for the respective LPAs were determined: 18:1 LPA at 435.2/152.8, DP=−40, CE=−28 and 20:4 LPA at 457.2/152.8, DP=−100, CE=−27).

The formation of 18:1 LPA was monitored and evaluated as ratio to 20:4 LPA.

TABLE 1

Biological data for compounds for the invention as obtained in Assay A.

| Example | Human ATX LPA $IC_{50}$ [nM] |
|---|---|
| 1.1 | 2.5 |
| 1.2 | 3.4 |
| 1.3 | 2.2 |
| 1.4 | 5.8 |
| 1.5 | 4.2 |
| 1.6 | 2.6 |
| 1.7 | 6.7 |
| 1.8 | 4.2 |
| 1.9 | 5.3 |
| 1.10 | 2.4 |
| 1.11 | 4.4 |
| 1.12 | 4.8 |
| 1.13 | 3.4 |

TABLE 2

Biological data for prior art compounds (examples 2 and 12 in WO2014/139882) as obtained in Assay A.

| Example in WO2014/139882 | Human ATX LPA $IC_{50}$ [nM] |
|---|---|
| 2 | 5 |
| 12 | 2 |

TABLE 3

Biological data for prior art compounds (example 19 in ACS Med. Chem. Lett. 2017, 8, 1252-1257) as obtained in Assay A.

| Example in ACS Med. Chem. Lett. 2017, 8, 1252-1257 | Human ATX LPA $IC_{50}$ [nM] |
|---|---|
| 19 | 2.2 |

Assay B: Whole-Blood ATX assay

45 µL human whole-blood was supplemented with 5 µL of the test compound, dissolved in phosphate-buffered saline (concentration range 0.12 nM-100 µM). This mixture was incubated for 1 h at 37° C. and stopped by addition of 100 µL 40 mM disodium hydrogen phosphate buffer containing 30 mM citric acid (pH 4) and 1 µM 17:0 LPA (internal standard). LPA was extracted by addition of 500 µL 1-butanol, followed by 10-min centrifugation at 4000 rpm, 4° C. From the resultant organic supernatant, a 200 µL aliquot was transferred into a 96-deep-well plate and transferred to the RapidFire-based MS/MS measurement.

The RapidFire autosampler was coupled to a binary pump (Agilent 1290) and a Triple Quad 6500 (ABSciex, Toronto, Canada). This system was equipped with a 10-µL loop, 5-µL Waters Atlantis HILIC cartridge (Waters, Elstree, UK), 90% acetonitrile containing 10 mM ammonium acetate as eluent A and 40% acetonitrile containing 10 mM ammoniumacetate as eluent B. For details see (Bretschneider et al., SLAS Discovery, 2017, 22, 425-432). The MS was operated in negative mode with a source temperature of 550° C., curtain gas=35, gas 1=65, and gas 2=80. The following transitions and MS parameters (DP: declustering potential and CE: collision energy) for the respective LPAs were determined: 18:2 LPA at 433.2/152.8, DP=−150, CE=−27 and 17:0 LPA at 423.5/152.8, DP=−100.

The formation of 18:2 LPA was monitored and evaluated as ratio to 17:0 LPA.

TABLE 4

Biological data for compounds for the invention as obtained in Assay B.

| Example | Human whole blood LPA $IC_{50}$ [nM] |
|---|---|
| 1.1 | 3.5 |
| 1.2 | 1.8 |
| 1.3 | 2.0 |
| 1.4 | 4.3 |
| 1.5 | 4.3 |
| 1.6 | 7.8 |
| 1.7 | 7.0 |
| 1.8 | 1.3 |
| 1.9 | 5.0 |
| 1.10 | 3.7 |
| 1.11 | 6.9 |
| 1.12 | 7.7 |
| 1.13 | 7.1 |

TABLE 5

Biological data for prior art compounds (examples 2 and 12 in WO2014/139882) as obtained in Assay B.

| Example in WO2014/139882 | Human whole blood LPA $IC_{50}$ [nM] |
|---|---|
| 2 | 370 |
| 12 | 50 |

TABLE 6

Biological data for prior art compounds (example 19 in ACS Med. Chem. Lett. 2017, 8, 1252-1257) as obtained in Assay B.

| Example in ACS Med. Chem. Lett. 2017, 8, 1252-1257 | Human whole blood LPA $IC_{50}$ [nM] |
|---|---|
| 19 | 29 |

Assay C: In Vivo

The test substance was solubilized in 0.5% natrosol supplemented with 0.015% Tween 80 for oral application to rats at a dose of 5 mg/kg. Blood samples were collected before compound administration and 8 hours post application on ice using EDTA as coagulation agent. Subsequently, plasma was prepared by centrifugation and stored until analysis at −20° C.

LPAs from plasma samples were extracted by using the procedure described by Scherer et al. (*Clinical chemistry* 2009, 55, 1218-22). 35 µL of heparinized plasma was mixed with 200 µL 40 mM disodium hydrogen phosphate buffer containing 30 mM citric acid (pH 4) and 1 µM 17:0 LPA (internal standard). Subsequently, 500 µL butanol was added and shaken vigorously for 10 min. Samples were centrifuged afterwards at 4000 rpm, 4° C., for 10 min. 500 µL of the organic upper phase was transferred to a fresh 96-deep-well plate and evaporated with a gentle nitrogen flow of 15 psi for 45 min. The resultant residual was dissolved in 100 µL ethanol prior to LC-MS analysis.

LC-MS Method for the Analytic of In Vivo Samples

A Triple Quad 6500 (ABSciex, Toronto, Canada) was equipped with an Agilent 1290 LC system (Agilent, Santa Clara, CA) a CTC autosampler and an Atlantis 50×2.1-mm, 3-µm HILIC LC column (Waters, Elstree, UK). Eluent A contained 0.2% formic acid and 50 mM ammonium formate in water, whereas eluent B consisted of 0.2% formic acid in acetonitrile. The LC gradient started from 95% solvent B and decreased within 1.5 min to 75% and within 0.2 min to 50% solvent B, with a further increase in the flow rate from 500 to 700 µL·min$^{-1}$. At 1.8 min, solvent B was set back to 95% and stayed constant for 0.7 min for re-equilibration of the column. The following LPA species were monitored (DP: declustering potential and CE: collision energy): 16:0 LPA at 409.2/152.8, DP=−150, CE=−28; 18:0 LPA at 437.3/152.8, DP=−60, CE=−28; 18:1 LPA at 435.2/152.8, DP=−40, CE=−28; 18:2 LPA at 433.2/152.8, DP=−150, CE=−28; 20:4 LPA at 457.2/152.8, DP=−100, CE=−29 and 17:0 LPA at 423.5/152.8, DP=−100, CE=−36. LPA depletion in percent was calculated based on the baseline LPA levels before test compound application. The sum of LPA refers to the species 16:0; 18:0; 18:1; 18:2 and 20:4

TABLE 7

Biological data for compounds for the invention as obtained in Assay C.

| Example | LPA reduction at 8 h [%] |
|---|---|
| 1.1 | 97.0 |
| 1.2 | 95.9 |
| 1.4 | 98.0 |
| 1.11 | 96.3 |

TABLE 8

Biological data for prior art compounds (examples 2 and 12 in WO2014/139882) as obtained in Assay C.

| Example | LPA reduction at 8 h [%] |
|---|---|
| 2 | 58.1 |
| 12 | 60.3 |

TABLE 9

Biological data for prior art compound (example 19 in ACS Med. Chem. Lett. 2017, 8, 1252-1257) as obtained in Assay C.

| Example | LPA reduction at 8 h [%] |
|---|---|
| 19 | 40.7 |

Method of Treatment

The present invention is directed to compounds of general formula (I) which are useful in the prevention and/or treatment of a disease and/or condition associated with or modulated by ATX and/or the biological activity of LPA, including but not limited to the treatment and/or prevention of inflammatory conditions, fibrotic diseases, conditions of the respiratory system, renal conditions, liver conditions, vascular and cardiovascular conditions, cancer, ocular conditions, metabolic conditions, cholestatic and other forms of chronic pruritus and acute and chronic organ transplant rejection and conditions of the nervous system. The compounds of general formula (I) are useful for the prevention and/or treatment of inflammatory conditions including, but not limited to Sjögren's syndrome, arthritis, osteoarthritis, multiple sclerosis, systemic lupus erythematousus, inflammatory bowel disease, inflammatory airways diseases such as chronic obstructive pulmonary disease (COPD) and chronic asthma; fibrotic diseases including, but not limited to interstitial lung diseases (ILDs) including Progressive Fibrosing Interstitial Lung Diseases (PFILDs) such as idiopathic pulmonary fibrosis (IPF), and SSC-ILD, familial interstitial lung disease myocardial and vascular fibrosis, renal fibrosis, liver fibrosis, pulmonary fibrosis, skin fibrosis, collagen vascular disease including Systemic Sclerosis (SSc) and encapsulating peritonitis; conditions of the respiratory system including, but not limited to diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), renal conditions including, but not limited to acute kidney injury and chronic renal disease with and without proteinuria including End-Stage Renal Disease (ESRD, focal segmental glomerular sclerosis, IgA nephropathy, vasculitides/systemic diseases as well as acute and chronic kidney transplant rejection; liver conditions including, but not limited to liver cirrhosis, hepatic congestion, cholestatic liver disease including pruritus, primary biliary cholangitis, non-alcoholic steatohepatitis and acute and chronic liver transplant rejection; vascular conditions including, but not limited to atherosclerosis, thrombotic vascular disease as well as thrombotic microangiopathies, proliferative arteriopathy (such as swollen myointimal cells surrounded by mucinous extracellular matrix and nodular thickening), endothelial dysfunction; cardiovascular conditions including, but not limited to acute coronary syndrome, coronary heart disease, myocardial infarction, arterial and pulmonary hypertension, cardiac arrhythmia such as atrial fibrillation, stroke and other vascular damage; cancer and cancer metastasis including, but not limited to breast cancer, ovarian cancer, lung cancer, prostate cancer, mesothelioma, glioma, hepatic carcinoma, gastrointestinal cancers and progression and metastatic aggressiveness thereof, ocular conditions including, but not limited to proliferative and non-proliferative (diabetic) retinopathy, dry and wet age-related macular degeneration (AMD), macular oedema, central arterial/venous occlusion, traumatic injury, glaucoma; metabolic conditions including, but not limited to obesity, dyslipidaemia and diabetes; conditions of the nervous system including, but not limited to neuropathic pain, Alzheimer's disease, schizophrenia, neuro-inflammation (for example, astrogliosis), peripheral and/or autonomic (diabetic) neuropathies.

Accordingly, the present invention relates to a compound of general formula (I) for use as a medicament.

Furthermore, the present invention relates to the use of a compound of general formula (I) for the treatment and/or prevention of a disease and/or condition associated with or modulated by ATX and/or the biological activity of LPA.

Furthermore, the present invention relates to the use of a compound of general formula (I) for the treatment and/or prevention of a disease and/or condition associated with or modulated by ATX and/or the biological activity of LPA, including but not limited to inflammatory conditions, fibrotic diseases, conditions of the respiratory system, renal conditions, liver conditions, vascular and cardiovascular conditions, cancer, ocular conditions, metabolic conditions, cholestatic and other forms of chronic pruritus and acute and chronic organ transplant rejection and conditions of the nervous system.

Furthermore, the present invention relates to the use of a compound of general formula (I) for the treatment and/or prevention of inflammatory conditions including, but not limited to Sjögren's syndrome, arthritis, osteoarthritis, multiple sclerosis, systemic lupus erythematousus, inflammatory bowel disease, inflammatory airways diseases such as chronic obstructive pulmonary disease (COPD) and chronic asthma; fibrotic diseases including, but not limited to interstitial lung diseases (ILDs) including Progressive Fibrosing Interstitial Lung Diseases (PFILDs) such as idiopathic pulmonary fibrosis (IPF), and SSC-ILD, familial interstitial lung disease myocardial and vascular fibrosis, renal fibrosis, liver fibrosis, pulmonary fibrosis, skin fibrosis, collagen vascular disease including Systemic Sclerosis (SSc) and encapsulating peritonitis; conditions of the respiratory system including, but not limited to diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), renal conditions including, but not limited to acute kidney injury and chronic renal disease with and without proteinuria including end-stage renal disease (ESRD, focal segmental glomerular sclerosis, IgA nephropathy, vasculitides/systemic diseases as well as acute and chronic kidney transplant rejection; liver conditions including, but not limited to liver cirrhosis, hepatic congestion, cholestatic liver disease including pruritus, primary biliary cholangitis, non-alcoholic steatohepatitis and acute and chronic liver transplant rejection; vascular conditions including, but not limited to atherosclerosis, thrombotic vascular disease as well as thrombotic microangiopathies, proliferative arteriopathy (such as swollen myointimal cells surrounded by mucinous extracellular matrix and nodular thickening), endothelial dysfunction; cardiovascular conditions including, but not limited to acute coronary syndrome, coronary heart disease, myocardial infarction, arterial and pulmonary hypertension, cardiac arrhythmia such as atrial fibrillation, stroke and other vascular damage; cancer and cancer metastasis including, but not limited to breast cancer, ovarian cancer, lung cancer, prostate cancer, mesothelioma, glioma, hepatic carcinoma, gastrointestinal cancers and progression and metastatic aggressiveness thereof, ocular conditions including, but not limited to proliferative and non-proliferative (diabetic) retinopathy, dry and wet age-related macular degeneration (AMD), macular oedema, central arterial/venous occlusion, traumatic injury, glaucoma; metabolic conditions including, but not limited to obesity, dyslipidaemia and diabetes; conditions of the nervous system including, but not limited to neuropathic pain, Alzheimer's disease, schizophrenia, neuro-inflammation (for example, astrogliosis), peripheral and/or autonomic (diabetic) neuropathies.

In a further aspect the present invention relates to a compound of general formula (I) for use in the treatment and/or prevention of above mentioned diseases and conditions.

In a further aspect the present invention relates to the use of a compound of general formula (I) for the preparation of a medicament for the treatment and/or prevention of above mentioned diseases and conditions.

In a further aspect of the present invention the present invention relates to methods for the treatment or prevention of above mentioned diseases and conditions, which method comprises the administration of an effective amount of a compound of general formula (I) to a human being.

Pharmaceutical Compositions

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc.

Suitable tablets may be obtained, for example, by mixing one or more compounds according to formula I with known excipients, for example inert diluents, carriers, disintegrants, adjuvants, surfactants, binders and/or lubricants.

Combination Therapy

Compounds according to the present invention can be combined with other treatment options known to be used in the art so that at least two active compounds in effective amounts are used to treat an indication for which the present invention is useful at the same time. Although combination therapy preferably includes the administration of two active compounds to the patient at the same time, it is not necessary that the compounds be administered to the patient at the same time, although effective amounts of the individual compounds will be present in the patient at the same time. Compounds according to the present invention may be administered with one or more combination partners as otherwise described herein.

Accordingly, the present invention provides a compound of formula (I) according to any of the preceding embodiments, characterised in that the compound of formula (I) is administered in addition to treatment with one or more anti-inflammatory molecules from the list consisting of IL6 modulators, anti-IL6R modulators and IL13/IL-4 JAKi modulators. According to another aspect, the present invention provides a compound of formula (I) according to any of the preceding embodiments, characterised in that the compound of formula (I) is administered in addition to treatment with one or more anti-fibrotic molecules from the list consisting of CB2 agonists, TGF modulators, FGFR modulators, VEGFR inhibitors, PDGFR inhibitors, FGF modulators, avP6 integrin modulators, anti-CTGF antibodies, ROCK2 inhibitors, rhPTX-2 (Pentraxin-2), JNK1 inhibitors, LOXL2 inhibitors, Galectin3 inhibitors, MK2 inhibitors, Wnt pathway inhibitors, TGFR inhibitors, PDE4 modulators, TRPA1 inhibitors and microRNA modulators.

According to another aspect, the present invention provides a compound of formula (I) according to any of the preceding embodiments, characterised in that the compound of formula (I) is administered in addition to nintedanib.

According to another aspect, the present invention provides a compound of formula (I) according to any of the preceding embodiments, characterised in that the compound of formula (I) is administered in addition to pirfenidone.

Preparation

The compounds according to the present invention may be obtained using methods of synthesis which are known to the one skilled in the art and described in the literature of organic synthesis. Preferably the compounds are obtained analogously to the methods of preparation explained more fully hereinafter, in particular as described in the experimental section.

The general processes for preparing the compounds according to the invention will become apparent to the one skilled in the art studying the following schemes. Starting materials may be prepared by methods that are described in the literature or herein, or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

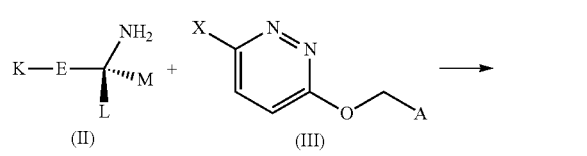

Compounds of general formula (I) are obtained by palladium-mediated Buchwald reactions or copper-mediated Ullmann reactions of pyridazinyl halogenides or triflates (III) with amines (II) wherein X is a leaving group such as Cl, Br, I or OTf (triflate).

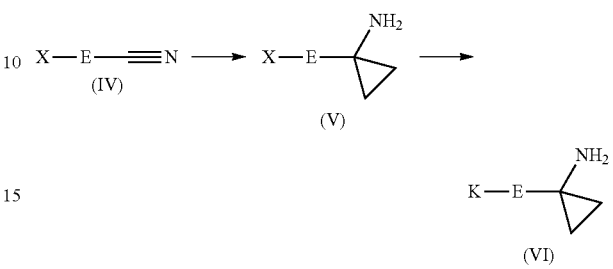

The synthesis route utilized for amines (II) is dependent on substituents L and M. For example, compounds of general formula (VI) are prepared from nitriles (IV) via Kulinkovich-Szymoniak-reaction to afford intermediates (V) wherein X is a leaving group which for example denotes Cl, Br, I or OTf (triflate), followed by palladium-mediated Buchwald reactions or copper-mediated Ullmann reactions of with amines (K).

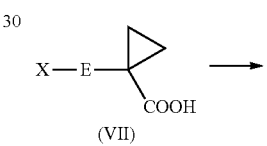

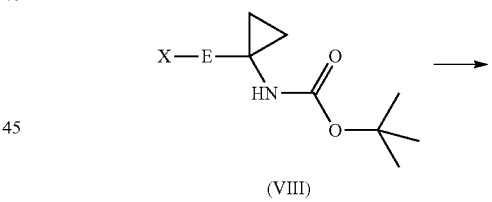

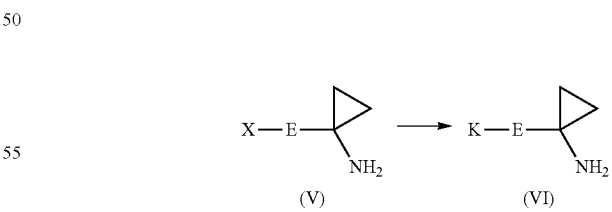

Alternatively, amines (II) are prepared from carboxylic acids (VII) by a Curtius rearrangement affording intermediates (VIII) followed by deprotection of the Boc-group to obtain amines (V). The latter can be transformed into amines (VI) by palladium-mediated Buchwald reactions or copper-mediated Ullmann reactions of aryl halogenides with amines (K) wherein X is a leaving group such as Cl, Br, I or OTf (triflate).

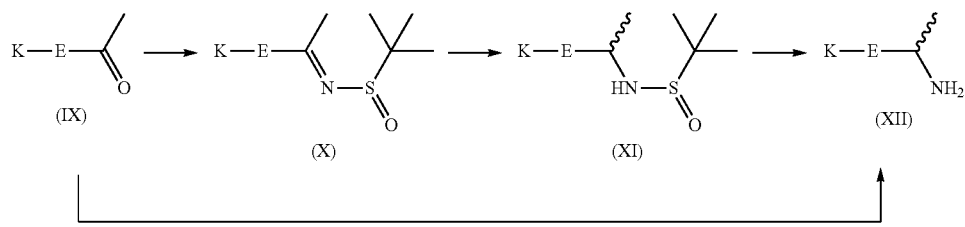

On the other hand, amines (XII) are obtained as racemic mixtures in one step by reductive amination of ketones (IX). They may also be prepared in enantiomerically pure form in a three-step process by condensation with an enantiomerically pure form of tert-butanesulfinamide to afford tert-butanesulfinyl imine (X). The latter is reduced to amines (XI). Subsequent cleavage of the N-tert-butanesulfinyl group with e.g. methanolic HCl provides amines (XII).

EXAMPLES

Experimental Part

The Examples that follow are intended to illustrate the present invention without restricting it. The terms "ambient temperature" and "room temperature" are used interchangeably and designate a temperature of about 20° C.

Abbreviations

| | |
|---|---|
| 9-BBN | 9-Borabicyclo(3.3.1)nonane |
| ACN | acetonitrile |
| ° C. | degree Celsius |
| conc. | concentrated |
| CuI | copper (I) iodide |
| Cy | cyclohexane |
| d | day |
| DCM | dichloromethane |
| DIPEA | N,N-diisopropylethylamine |
| DMF | N,N-dimethylformamide |
| DMSO | dimethyl sulfoxide |
| dppf | 1,1'-Bis(diphenylphosphino)ferrocene |
| EE | ethyl acetate |
| ESI-MS | electrospray ionisation mass spectrometry |
| EtOAc | ethyl acetate |
| Ex. | example |
| Eq | equivalent |
| g | gramm |
| h | hour |
| HCl | hydrogen chloride |
| HPLC | high performance liquid chromatography |
| $K_2CO_3$ | potassium carbonate |
| L | liter |
| M | molar weight/g/mol |
| MeOH | methanol |
| mg | milligramm |
| $MgSO_4$ | magnesium sulfate |
| min | minute |
| mL | milliliter |
| mmol | millimol |
| N | 1 mol/L |
| NaCl | sodium chloride |
| NaH | sodium hydride |
| $NaHCO_3$ | sodium bicarbonate |
| NaOH | sodium hydroxide |
| NaOtBu | sodium tert-butoxide |
| $Na_2SO_4$ | sodium sulfate |
| $Na_2S_2O_3$ | sodium thiosulfate |
| $Na_2SO_4$ | sodium sulfate |
| $NH_4Cl$ | ammonium chloride |
| $NH_4OH$ | ammonium hydroxide |
| NMP | N-Methyl-2-pyrrolidone |
| No. | number |

| | |
|---|---|
| Pd₂(dba)3 | Tris(dibenzylideneacetone)dipalladium(0) |
| PTK | phase-transfer-cartridge |
| RP | reversed phase |
| RT | room temperature (about 20° C.) |
| Rt | retention time |
| RUPHOS palladacycle | chloro-(2-dicyclohexylphosphino-2',6'-diisopropoxy-1,1'-biphenyl)[2-(2-aminoethyl)phenyl]palladium(II)-methyl-t-butyl ether adduct |
| SFC | supercritical fluid chromatography |
| tBME | tert-butylmethylether |
| TFA | trifluoroacetic acid |
| THF | tetrahydrofuran |
| Vol.-% | volume percent |
| XPHOS Pd G3 | (2-dicyclohexylphosphino-2',4',6'-triisopropyl-1,1'-biphenyl)[2-(2'-amino-1,1'-biphenyl)]palladium(II) methanesulfonate |

Preparation of Starting Compounds

Example I

Example I.1

3-{[6-(Difluoromethyl)pyridin-3-yl]methoxy}-6-iodopyridazine

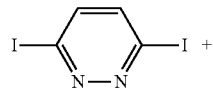 +

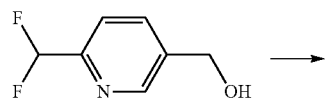 →

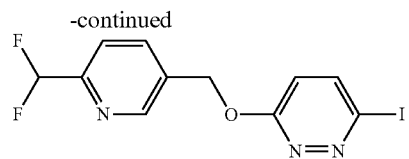

17.7 g (53.3 mmol) 3,6-Diiodopyridazine (CAS-No. 20698-04-8) and 8.50 g (53.41 mmol) [6-(difluoromethyl)pyridin-3-yl]methanol (CAS-No. 946578-33-2) in 25 mL THF are cooled to 0° C. and 2.33 g (53.3 mmol) sodium hydride (55% purity) is added. The reaction mixture is stirred at RT overnight and concentrated under reduced pressure. The residue is diluted with water. The precipitate is filtered, washed with water and tBME and dried at 50° C. in vacuo overnight to afford 17.5 g product.

$C_{11}H_8F_2IN_3O$ (M=363.1 g/mol)
ESI-MS: 364 [M+H]⁺
$R_t$ (HPLC): 0.90 min (method A)

The following compounds are prepared according to the general procedure (example I.1) described above:

| Ex. | Starting material | Structure | Reaction conditions | ESI-MS | HPLC retention time (method) [min] |
|---|---|---|---|---|---|
| I.2 | [structure shown] | [structure shown] | 1.1 eq NaH; 0° C. to RT | 382 [M + H]⁺ | 0.99 (B) |

Example II

1-(6-Bromopyridin-3-yl)cyclopropan-1-amine

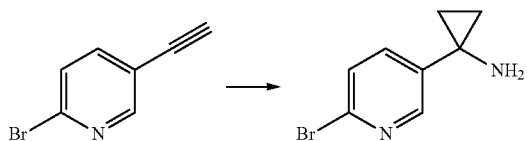

732 mg (4.00 mmol) 6-Bromopyridine-3-carbonitrile (CAS No. 139585-70-9) is diluted with 30 mL diethylether and 1.37 mL (4.67 mmol) titantetraisopropylate is added dropwise at RT. To the mixture is added 2.95 mL (8.84 mmol) ethylmagnesiumbromide (3 M in diethylether) under cooling at 15-20° C. The reaction mixture is stirred at RT for 30 min. Under cooling 1.26 mL (9.97 mmol) borotrifluoride-diethyletherate is added to the mixture and it is stirred at RT for 45 min. The reaction mixture is quenched with 20 mL 2 N NaOH under cooling, stirred at RT for 2 h and filtered through celite. The filter cake is washed with diethylether. The water phase of the filtrate is extracted with diethylether and all of the organic layers are reduced in vacuo. The residue is purified by HPLC to afford 203 mg of the product.

$C_8H_9BrN_2$ (M=436.3 g/mol)
ESI-MS: 214/216 Br $[M+H]^+$
Rt (HPLC): 0.92 min (method B)

Example III

[1-(4-Bromo-2-fluoro-phenyl)-cyclopropyl]-carbamic acid tert-butyl ester

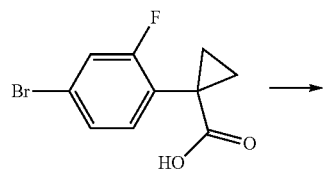

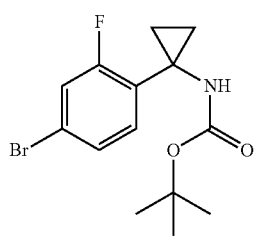

0.50 g (1.93 mmol) 1-(4-bromo-2-fluorophenyl) cyclopropane-1-carboxylic acid (CAS Nr. 872422-15-6) in 5 mL tert-butanol under argon atmosphere is treated with 0.43 mL (2.51 mmol) DIPEA and 0.50 mL (2.32 mmol) diphenylphosphoryl azide. The reaction mixture is refluxed overnight. The reaction mixture is concentrated under reduced pressure. The residue is dissolved in 200 mL ethyl acetate; the organic phase is washed with 150 mL 5% citric acid, saturated NaHCO₃-solution, saturated NaCl-solution, dried and evaporated to the crude product. The residue is purified by column chromatography (silica gel: Cy/EE=4/1) to afford 541 mg of the product.

$C_{14}H_{17}BrFNO_2$ (M=330.2 g/mol)
ESI-MS: 331/333 Br $[M+H]^+$
$R_t$ (HPLC): 1.17 min (method D)

Example IV

Example IV.1 tert-Butyl N-{1-[4-(4-acetylpiperazin-1-yl)phenyl]cyclopropyl}carbamate

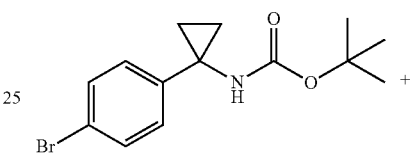

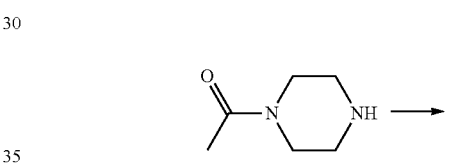

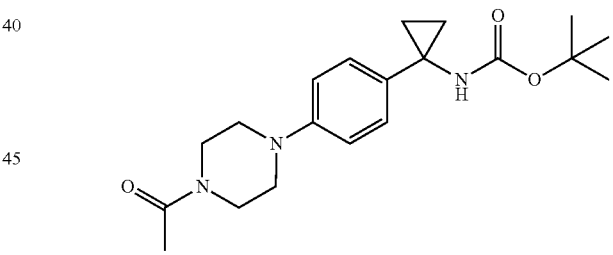

4.50 g (14.4 mmol) tert-Butyl N-[1-(4-bromophenyl)cyclopropyl]carbamate (CAS No. 360773-84-8), 2.22 g (17.3 mmol) 1-(piperazin-1-yl)ethan-1-one (CAS No. 13889-98-0), 0.18 g (0.22 mmol) RUPHOS palladacycle (CAS No. 1028206-60-1) and 2.08 g (21.6 mmol) sodium tert-butoxide in 50 mL 1,4-dioxane are stirred at 80° C. for 10 min. The reaction mixture is diluted with EtOAc and washed with semi conc. K₂CO₃-solution. The organic layer is dried with Na₂SO₄ and concentrated in vacuo. The residue is purified by column chromatography (silica gel; DCM/MeOH (95:05)) to afford 3.30 g product.

$C_{20}H_{29}N_3O_3$ (M=359.5 g/mol)
ESI-MS: 360 $[M+H]^+$
$R_t$ (HPLC): 0.71 min (method D)

The following compounds are prepared according to the general procedure (example IV. 1) described above:

| Ex. | Starting material | Structure | Reaction conditions | ESI-MS | HPLC retention time (method) [min] |
|---|---|---|---|---|---|
| IV.2 | 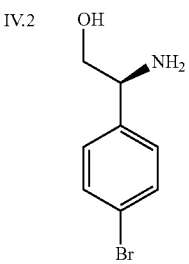 | 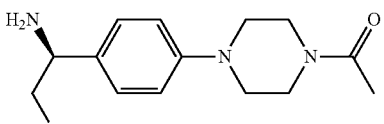 | 4 eq NaOtBu; 0.03 eq catalyst; 100° C. | 247 [M + H − NH$_3$]$^+$ | 0.58 (A) |
| IV.3 | 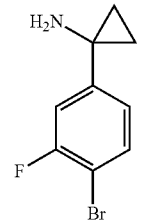 | 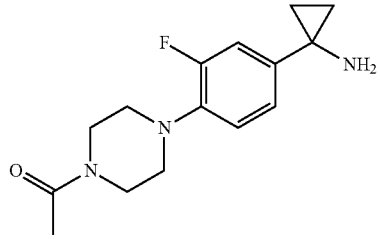 | 0.1 eq catalyst; 0.1 eq Ruphos as ligand; 3 min; directly purified by HPLC | 261 [M + H − NH$_3$]$^+$ | 0.76 (A) |
| IV.4 | II | 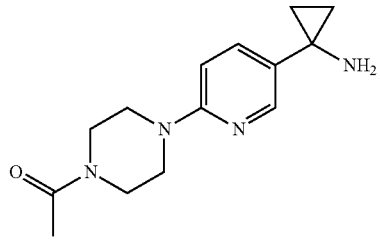 | neutralization of the amine; 0.1 eq catalyst; 0.1 eq Ruphos; purified by HPLC | 244 [M + H − NH$_3$]$^+$ | 0.88 (A) |
| IV.5 | 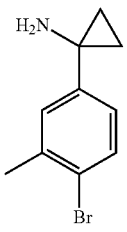 | 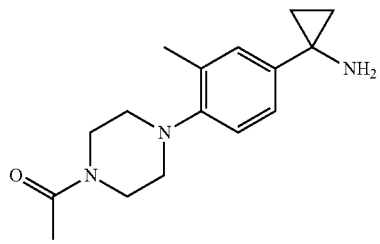 [SMILES: CC(=O)N1CCN(c2ccc(C3(N)CC3)cc2C)CC1] | 0.02 eq catalyst; 2 eq NaOtBu; 15 min 80° C., RT over weekend; directly purified by HPLC | 274 [M + H]$^+$ | 0.72 (B) |
| IV.6 | III | 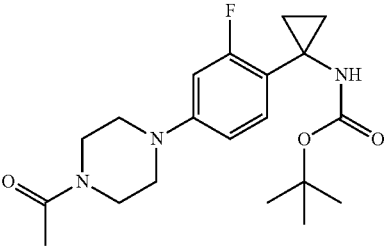 [SMILES: CC(=O)N1CCN(c2ccc(C3(NC(=O)OC(C)(C)C)CC3)c(F)c2)CC1] | 1 eq carbamate; 2 eq piperazine; 1.5 eq NaOtBu; 0.04 eq catalyst | 378 [M + H]$^+$ | 0.96 (D) |

Example V

Example V.1

1-{4-[4-(1-aminocyclopropyl)phenyl]piperazin-1-yl}ethan-1-one

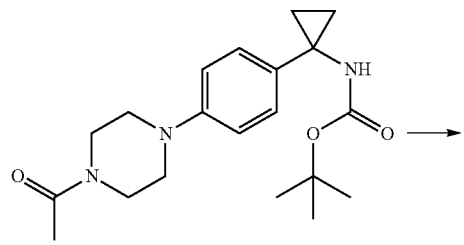

2.42 g (6.73 mmol) tert-Butyl 2-(4-cyanophenyl)-2,7-diazaspiro[3.5]nonane-7-carboxylate (example IV.1) is diluted with 50 mL DCM and 5 mL TFA is added. The reaction mixture is stirred at RT overnight. The mixture is evaporated and the residue is dissolved in MeOH. The solution is basified with NaHCO$_3$, filtered and evaporated. The crude product is purified by column chromatography (silica gel; DCM/MeOH/NH$_3$ (9:1:0.1)), followed by purification with HPLC to afford 650 mg product.

C$_{15}$H$_{21}$N$_3$O (M=259.3 g/mol)
ESI-MS: 260 [M+H]$^+$
R$_t$ (HPLC): 0.72 min (method A)

The following compounds are prepared according to the general procedure (example V.1) described above:

Example VI

Example VI.1

N-{1-[4-(1-Aminocyclopropyl)phenyl]piperidin-4-yl}-N-methylacetamide

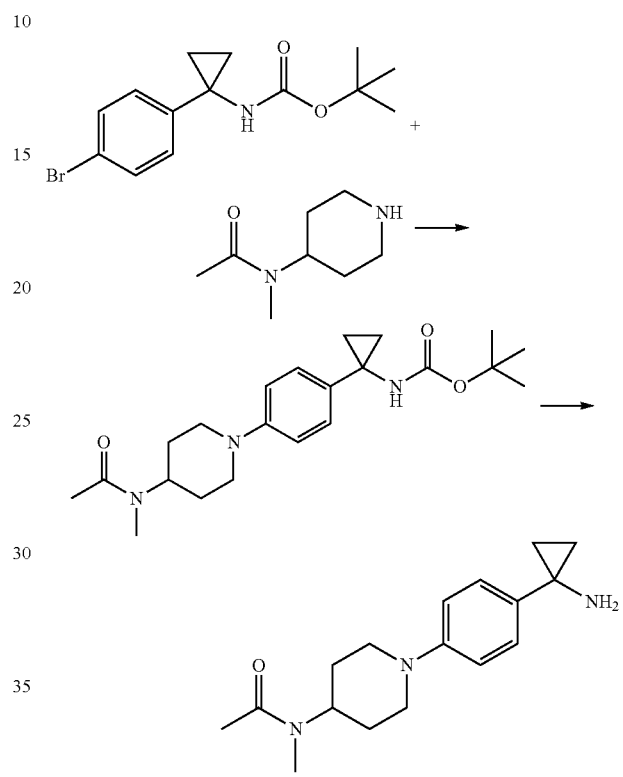

380 mg (1.22 mmol) tert-Butyl N-[1-(4-bromophenyl)cyclopropyl]carbamate (CAS No. 360773-84-8) and 570 mg (3.65 mmol) N-methyl-N-(piperidin-4-yl)acetamide (CAS No. 83180-55-6) are diluted with 1,4-dioxane and 870 mg (2.68 mmol) cesium carbonate and 50 mg (0.06 mmol) XPHOS Pd G3 are added. The reaction mixture is stirred at 80° C. for 2.5 h, filtered and diluted with EtOAc. The organic layer is washed with semi conc. Na—HCO$_3$-solution, dried with PTK and concentrated under reduced pressure. The residue is purified by HPLC. The crude intermediate is dissolved with 2 mL 4 N HCl in 1,4-dioxane and the

| Ex. | Starting material | Structure | ESI-MS | HPLC retention time (method) [min] |
|---|---|---|---|---|
| V.2 | (F-substituted piperazine-phenyl-cyclopropyl-NH-Boc) | (F-substituted piperazine-phenyl-cyclopropyl-NH$_2$) | 261 [M + H]$^+$ | 0.76 (D) | mixture is stirred at RT for 30 min. The reaction mixture is evaporated in vacuo and the residue is purified by HPLC to get 48.0 mg of the product.

$C_{17}H_{25}N_3O$ (M=287.4 g/mol)
ESI-MS: 288 [M+H]$^+$
Rt (HPLC): 0.78 min (method A)

The following compounds are prepared according to the general procedure (example VI.1) described above:

| Ex. | Starting material | Structure | Reaction conditions | ESI-MS | HPLC retention time (method) [min] |
|---|---|---|---|---|---|
| VI.2 | 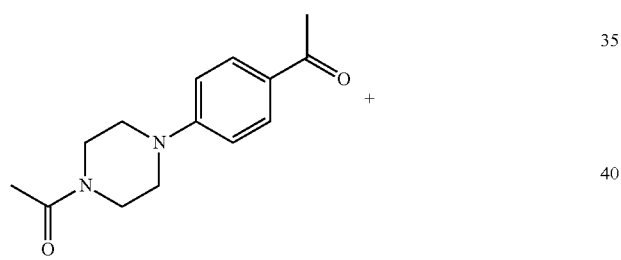 | 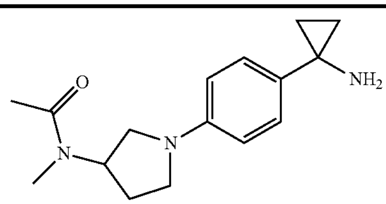 | 2.5 eq pyrrolidine | 274 [M + H]$^+$ | 0.77 (A) |

Example VII

Example VII.1

(R)—N-[(1E)-1-[4-(4-Acetylpiperazin-1-yl)phenyl]ethylidene]-2-methylpropane-2-sulfinamide

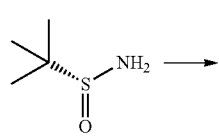

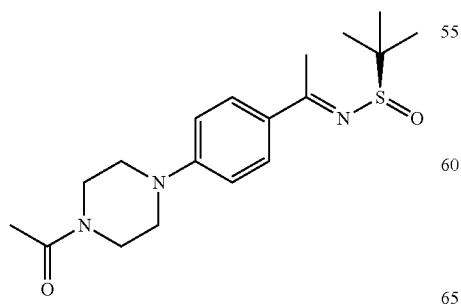

A mixture of 1.00 g (4.06 mmol) 1-[4-(4-acetylphenyl) piperazin-1-yl]ethan-1-one (CAS No. 104080-54-8), 0.98 g (8.12 mmol) (R)-2-methylpropane-2-sulfinamide (CAS No. 196929-78-9) and 2.97 mL (12.2 mmol) titanium ethoxide (85%) in 10 mL THF is stirred at 80° C. overnight. After cooling the reaction mixture is diluted with semi conc. NaCl-solution and EtOAc. The precipitate is filtered and the two layers of the filtrate are separated. The organic layer is dried with $Na_2SO_4$ and evaporated under reduced pressure. The residue is purified by column chromatography (silica gel, DCM/MeOH (9:1)) to afford 1.30 g product.

$C_{18}H_{27}N_3O_2S$ (M=349.5 g/mol)
ESI-MS: 350 $[M+H]^+$
$R_t$ (HPLC): 0.91 min (method D)

The following compound is prepared according to the general procedure (example VII.1) described above:

| Ex. | Starting material | Structure | ESI-MS | HPLC retention time (method) [min] |
|---|---|---|---|---|
| VII.2 | | 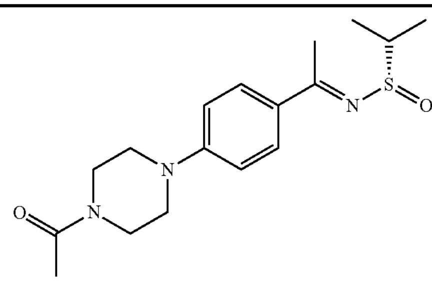 | 350 $[M + H]^+$ | 0.91 (B) |

Example VIII

Example VIII.1

(R)—N-[(1R)-1-[4-(4-Acetylpiperazin-1-yl)phenyl] ethyl]-2-methylpropane-2-sulfinamide

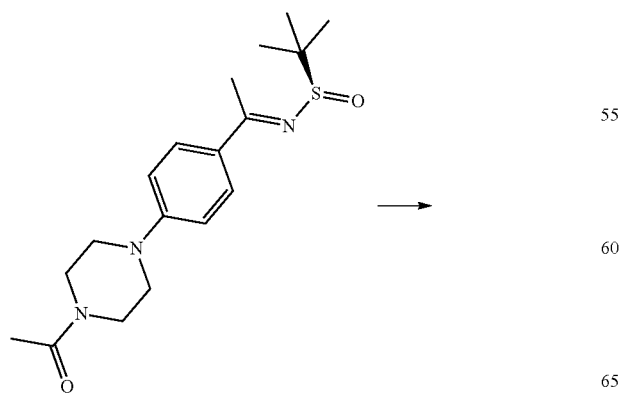

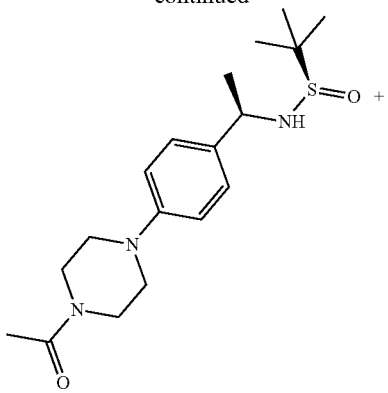

+

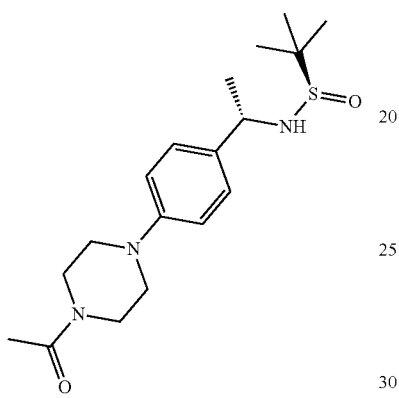

To a solution of 1.30 g (3.72 mmol) (R)—N-[(1E)-1-[4-(4-acetylpiperazin-1-yl)phenyl]-ethylidene]-2-methylpropane-2-sulfinamide (example VII.1) in 2 mL THF is added water and cooled to −50° C. The reaction mixture is treated with 0.42 g (11.2 mmol) sodium borohydride and is warmed to RT. Semi conc. NaHCO$_3$-solution is added to the mixture and the organic phase is separated, dried and concentrated in vacuo. The residue is purified by HPLC to afford 0.50 g of the desired diastereomer.

$C_{18}H_{29}N_3O_2S$ (M=351.5 g/mol)
ESI-MS: 352 [M+H]$^+$
R$_t$ (HPLC): 0.82 min (method D)

The following compound is prepared according to the general procedure (example VIII.1) described above:

| Ex. | Starting material | Structure | Reaction conditions | ESI-MS | HPLC retention time (method) [min] |
|---|---|---|---|---|---|
| VIII.2 | VII.2 | 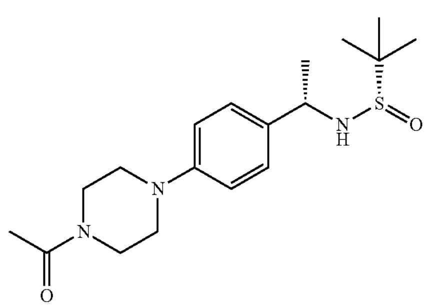 [SMILES: CC(=O)N1CCN(c2ccc([C@H](C)N[S@@](=O)C(C)(C)C)cc2)CC1] | purification: column chromatography on silica gel and RP-HPLC | 352 [M + H]$^+$ | 0.83 (A) |

Example IX

Example IX.1

1-(4-{4-[(1R)-1-Aminoethyl]phenyl}piperazin-1-yl)ethan-1-one

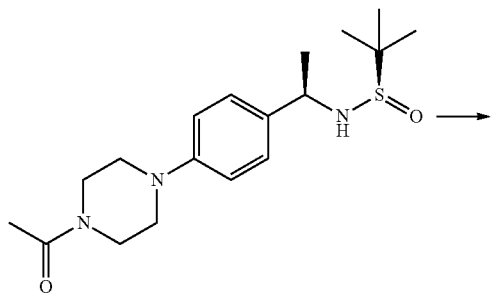

550 mg (1.56 mmol) (R)—N-[(1R)-1-[4-(4-Acetylpiperazin-1-yl)phenyl]ethyl]-2-methyl-propane-2-sulfinamide (example VIII. 1) is dissolved in 10 mL THF and treated with 0.98 mL (3.91 mmol) 4 N hydrogen chloride in 1,4-dioxane. The reaction mixture is stirred at RT for 30 min. The precipitate is filtered and washed with THF. The solid is dissolved in MeOH and a basic resin is added. The resin is filtered off and the filtrate is evaporated under reduced pressure to afford 0.33 g product.

$C_{14}H_{21}N_3O$ (M=247.3 g/mol)
ESI-MS: 231 [M+H–NH$_3$]$^+$
$R_t$ (HPLC): 0.59 min (method D)

The following compound is prepared according to the general procedure (example IX.1) described above:

| Ex. | Starting material | Structure | Reaction conditions | ESI-MS | HPLC retention time (method) [min] |
|---|---|---|---|---|---|
| IX.2 | VIII.2 | 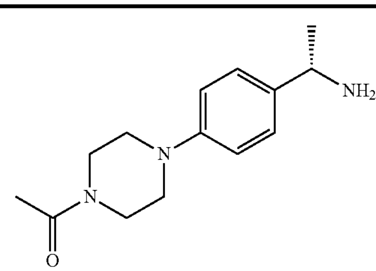 | 2.8 eq HCl; | 231 [M + H – NH$_3$]$^+$ | 0.59 (D) |

Example X

1-{4-[4-(1-Aminoethyl)phenyl]piperazin-1-yl}ethan-1-one

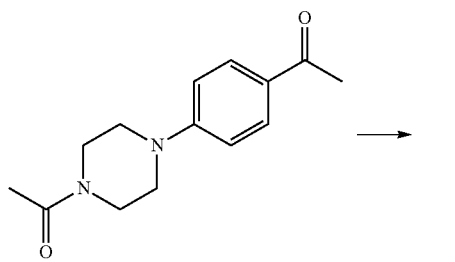

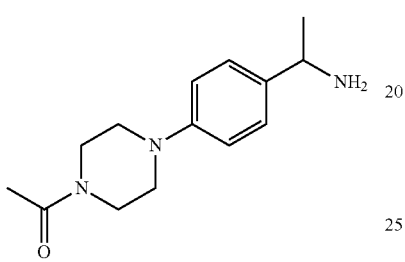

0.90 g (3.65 mmol) 1-[4-(4-Acetylpiperazin-1-yl)phenyl]ethan-1-one (CAS No. 104080-54-8) in 10 mL MeOH is treated with 2.82 g (36.54 mmol) ammonium acetate and 0.28 g (4.38 mmol) sodium cyanoborohydride. The reaction mixture is stirred at 80° C. for 1 h, diluted with methyl-THF and washed with conc. $K_2CO_3$-solution. The organic phase is dried with $Na_2SO_4$ and reduced to dryness in vacuo to get 650 mg of the product.

$C_{14}H_{21}N_3O$ (M=247.3 g/mol)

ESI-MS: 231 $[M+H-NH_3]^+$ $R_t$ (HPLC): 0.69 min (method A)

Preparation of Final Compounds

Example 1.1

1-[4-(4-{1-[(6-{[6-(trifluoromethyl)pyridin-3-yl]methoxy}pyridazin-3-yl)amino]cyclopropyl}phenyl)piperazin-1-yl]ethan-1-one

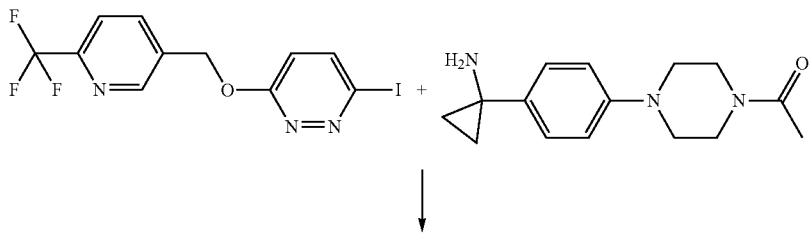

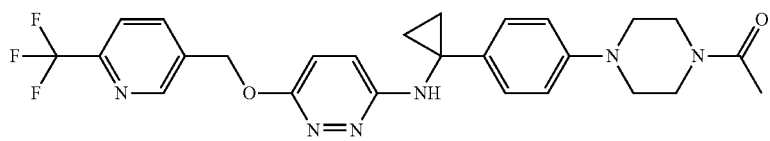

A mixture of 106 mg (0.28 mmol) 3-iodo-6-{[6-(trifluoromethyl)pyridin-3-yl]methoxy}-pyridazine (example 1.2), 60.0 mg (0.23 mmol) 1-{4-[4-(1-aminocyclopropyl)phenyl]-piperazin-1-yl}ethan-1-one (example V.1), 8.8 mg (46.3 µmol) copper iodide, 18.6 mg (0.09 mmol) [(2,6-difluorophenyl)carbamoyl]formic acid (CAS No. 1018295-42-5) and 147 mg (0.69 mmol) potassium phosphate in 3 mL DMSO is stirred at 80° C. After 15 min the reaction mixture is diluted with EtOAc and washed with a solution of NH$_4$Cl/ammonia-solution (9:1). The organic phase is dried with Na$_2$SO$_4$ and reduced in vacuo. The residue is purified by HPLC to afford 23.0 mg of the product.

C$_{26}$H$_{27}$F$_3$N$_6$O$_2$ (M=512.5 g/mol)
ESI-MS: 513 [M+H]$^+$
R$_t$ (HPLC): 0.79 min (method A)
$^1$H NMR (400 MHz, DMSO-d$_6$) δ 8.84 (d, J=1.14 Hz, 1H), 8.13 (dd, J=1.46, 8.05 Hz, 1H), 7.91 (d, J=7.98 Hz, 1H), 7.54 (s, 1H), 7.07 (d, J=8.74 Hz, 1H), 7.00 (d, J=9.51 Hz, 1H), 6.89 (s, 1H), 6.79-6.88 (m, 3H), 5.47 (s, 2H), 3.54 (br d, J=3.30 Hz, 4H), 3.04-3.10 (m, 2H), 2.96-3.04 (m, 2H), 2.02 (s, 3H), 1.14-1.23 (m, 2H), 1.08-1.14 (m, 2H)

The following compounds are prepared according to the general procedure (example 1.1) described above:

| Ex. | Structure |
|-----|-----------|
| 1.2 | 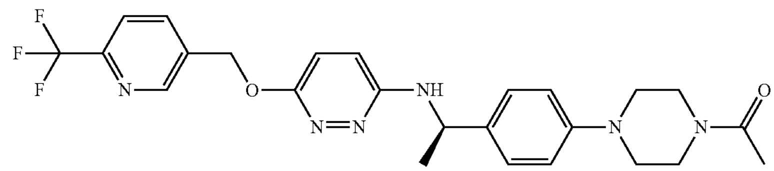 [SMILES: CC(=O)N1CCN(c2ccc([C@@H](C)Nc3ccc(OCc4ccc(C(F)(F)F)nc4)nn3)cc2)CC1] |
| 1.3 | 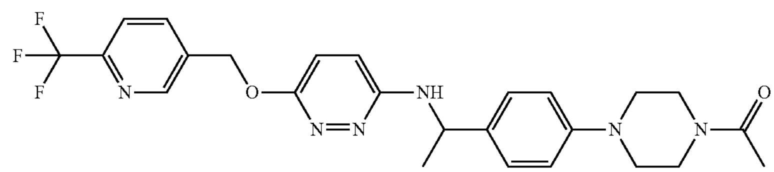 [SMILES: CC(=O)N1CCN(c2ccc(C(C)Nc3ccc(OCc4ccc(C(F)(F)F)nc4)nn3)cc2)CC1] |
| 1.4 | 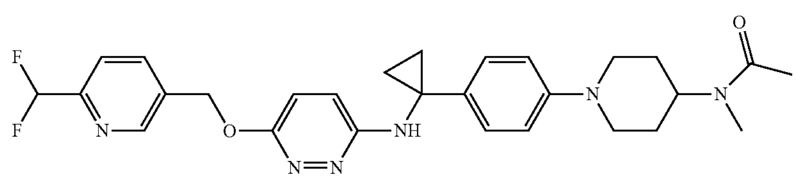 [SMILES: CC(=O)N(C)C1CCN(c2ccc(C3(Nc4ccc(OCc5ccc(C(F)F)nc5)nn4)CC3)cc2)CC1] |
| 1.5 | 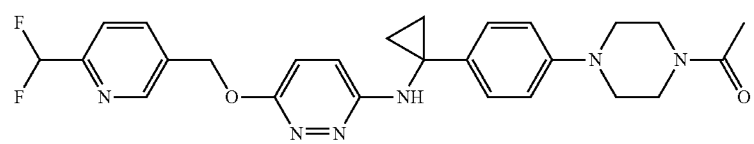 [SMILES: CC(=O)N1CCN(c2ccc(C3(Nc4ccc(OCc5ccc(C(F)F)nc5)nn4)CC3)cc2)CC1] |
| 1.6 | 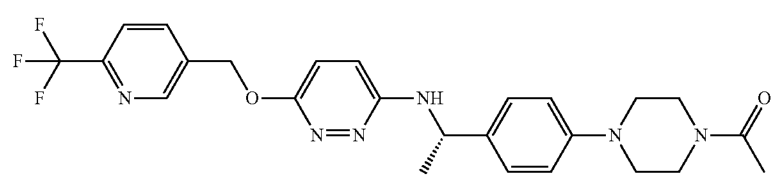 [SMILES: CC(=O)N1CCN(c2ccc([C@H](C)Nc3ccc(OCc4ccc(C(F)(F)F)nc4)nn3)cc2)CC1] |
| 1.7 | 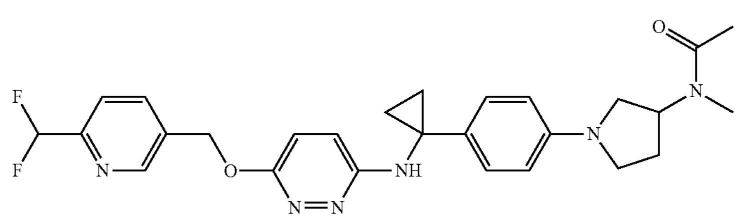 [SMILES: CC(=O)N(C)C1CCN(c2ccc(C3(Nc4ccc(OCc5ccc(C(F)F)nc5)nn4)CC3)cc2)C1] |
| 1.8 | 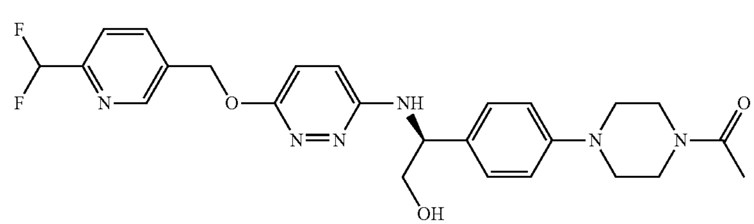 [SMILES: CC(=O)N1CCN(c2ccc([C@@H](CO)Nc3ccc(OCc4ccc(C(F)F)nc4)nn3)cc2)CC1] |

-continued

| Ex. | Structure |
|---|---|
| 1.9 | [structure: 6-(trifluoromethyl)pyridin-3-yl-CH2-O-pyridazine-NH-CH(CH2OH)-phenyl-piperazine-acetyl] |
| 1.10 | [structure: 6-(trifluoromethyl)pyridin-3-yl-CH2-O-pyridazine-NH-C(cyclopropyl)-(3-fluorophenyl)-piperazine-acetyl] |
| 1.11 | [structure: 6-(trifluoromethyl)pyridin-3-yl-CH2-O-pyridazine-NH-C(cyclopropyl)-pyridine-piperazine-acetyl] |
| 1.12 | [structure: 6-(trifluoromethyl)pyridin-3-yl-CH2-O-pyridazine-NH-C(cyclopropyl)-(2-fluorophenyl)-piperazine-acetyl] |
| 1.13 | [structure: 6-(trifluoromethyl)pyridin-3-yl-CH2-O-pyridazine-NH-C(cyclopropyl)-(2-methylphenyl)-piperazine-acetyl] |

| Ex. | Starting materials | | Reaction conditions | ESI-MS | HPLC retention time (method) [min] |
|---|---|---|---|---|---|
| 1.2 | I.2 | IX.1 | 1.1 eq iodide; 110° C.; 10 min | 501 [M + H]+ | 0.97 (A) |
| 1.3 | I.2 | X | 1.25 eq iodide; 110° C.; 45 min | 501 [M + H]+ | 0.78 (D) |
| 1.4 | I.1 | VI.1 | 120° C.; 20 min | 523 [M + H]+ | 0.96 (A) |
| 1.5 | I.1 | V | 40 min | 495 [M + H]+ | 0.91 (A) |
| 1.6 | I.2 | IX.2 | 1.1 eq iodide; 110° C.; 10 min | 501 [M + H]+ | 0.97 (A) |
| 1.7 | I.1 | VI.2 | 1.2 eq iodide; 120° C.; 1 h | 509 [M + H]+ | 0.80 (D) |
| 1.8 | I.1 | IV.2 | 1 eq iodide; 1.1 eq amine; 0.4 eq CuI; 110° C.; 10 min | 499 [M + H]+ | 0.70 (D) |
| 1.9 | I.2 | IV.2 | 1 eq iodide; 110° C.; 10 min | 517 [M + H]+ | 0.74 (D) |
| 1.10 | I.2 | IV.3 | 1.1 eq iodide; 0.8 eq CuI; 50° C.; 2 h | 531 [M + H]+ | 0.80 (C) |
| 1.11 | I.2 | IV.4 | 0.8 eq CuI; 0.4 eq ligand; 80° C.; 15 min | 514 [M + H]+ | 0.97 (D) |
| 1.12 | I.2 | V.II | 0.8 eq CuI; 3 eq base; 0.4 eq ligand; 70° C.; 1 h; directly purified by HPLC | 531 [M + H]+ | 0.82 (D) |
| 1.13 | I.2 | IV.5 | 0.2 eq CuI; 3 eq base; 0.4 eq ligand; 60° C. over-night; directly purified by HPLC | 527 [M + H]+ | 0.89 (B) |

| Ex. | ¹H-NMR data |
|---|---|
| 1.2 | ¹H NMR (400 MHz, DMSO-$d_6$) δ 8.82 (d, J = 1.01 Hz, 1H), 8.11 (dd, J = 1.46, 8.05 Hz, 1H), 7.91 (d, J = 8.11 Hz, 1H), 7.22 (d, J = 8.74 Hz, 2H), 6.90-7.01 (m, 2H), 6.83-6.91 (m, 3H), 5.45 (d, J = 2.53 Hz, 2H), 4.94 (t, J = 7.10 Hz, 1H), 3.47-3.60 (m, 4H), 3.06-3.15 (m, 2H), 2.99-3.06 (m, 2H), 2.03 (s, 3H), 1.40 (d, J = 6.84 Hz, 3H) |
| 1.3 | ¹H NMR (400 MHz, DMSO-$d_6$) δ 8.82 (d, J = 1.52 Hz, 1H), 8.11 (dd, J = 1.46, 8.05 Hz, 1H), 7.91 (d, J = 8.11 Hz, 1H), 7.22 (d, J = 8.74 Hz, 2H), 6.95 (d, J = 8.11 Hz, 2H), 6.89 (d, J = 8.74 Hz, 3H), 5.45 (d, J = 2.66 Hz, 2H), 4.94 (t, J = 7.16 Hz, 1H), 3.52-3.61 (m, 4H), 3.06-3.13 (m, 2H), 2.97-3.06 (m, 2H), 2.03 (s, 3H), 1.40 (d, J = 6.84 Hz, 3H) |
| 1.4 | ¹H NMR (400 MHz, DMSO-$d_6$) δ 8.75 (d, J = 1.52 Hz, 1H), 8.06 (d, J = 2.03 Hz, 1H), 8.04 (d, J = 2.03 Hz, 1H), 7.71 (d, J = 8.11 Hz, 1H), 7.52 (s, 1H), 7.04 (d, J = 8.74 Hz, 2H), 7.00 (s, 1H), 6.96 (d, J = 8.74 Hz, 1H), 6.88-7.11 (t, 1H), 6.86 (s, 1H), 6.80-6.85 (m, 2H), 5.43 (s, 2H), 4.31-4.41 (m, 1H), 3.67 (br d, J = 10.52 Hz, 2H), 2.80 (s, 2H), 2.66 (s, 2H), 2.05 (s, 1H), 1.98 (s, 2H), 1.82 (br d, J = 3.68 Hz, 1H), 1.76-1.80 (m, 1H), 1.72 (br dd, J = 3.93, 12.29 Hz, 1H), 1.67 (br d, J = 3.04 Hz, 1H), 1.45-1.55 (m, 1H), 1.07-1.19 (m, 2H) |
| 1.5 | ¹H NMR (400 MHz, DMSO-$d_6$) δ 8.75 (d, J = 1.39 Hz, 1H), 8.05 (dd, J = 1.96, 8.05 Hz, 1H), 7.71 (d, J = 7.98 Hz, 1H), 7.53 (s, 1H), 7.07 (d, J = 8.74 Hz, 2H), 6.94-7.00 (t, 2H), 6.88 (s, 1H), 6.85 (d, J = 2.41 Hz, 1H), 6.83 (s, 1H), 5.43 (s, 2H), 3.54 (br s, 4H), 3.05-3.10 (m, 2H), 2.98-3.03 (m, 1H), 2.98-3.03 (m, 1H), 2.02 (s, 3H), 1.15-1.19 (m, 2H), 1.09-1.14 (m, 2H) |
| 1.6 | ¹H NMR (400 MHz, DMSO-$d_6$) δ 8.82 (d, J = 1.27 Hz, 1H), 8.11 (dd, J = 1.39, 8.11 Hz, 1H), 7.91 (d, J = 7.98 Hz, 1H), 7.22 (d, J = 8.74 Hz, 2H), 6.95 (d, J = 8.24 Hz, 2H), 6.89 (d, J = 8.62 Hz, 3H), 5.45 (d, J = 2.53 Hz, 2H), 4.94 (t, J = 7.10 Hz, 1H), 3.51-3.59 (m, 4H), 3.06-3.13 (m, 2H), 3.00-3.06 (m, 2H), 2.03 (s, 3H), 1.40 (d, J = 6.84 Hz, 3H) |
| 1.7 | ¹H NMR (400 MHz, DMSO-$d_6$) δ 8.79 (s, 1H), 8.09 (d, J = 8.49 Hz, 1H), 7.75 (d, J = 7.98 Hz, 1H), 7.41-7.61 (m, 2H), 7.06 (br d, J = 8.36 Hz, 2H), 6.81-7.13 (t, 1H), 6.47-6.57 (m, 2H), 5.42 (s, 2H), 5.16 (br t, J = 7.22 Hz, 1H), 4.59-4.68 (m, 1H), 3.24-3.31 (m, 2H), 3.06-3.23 (m, 2H), 2.86 (s, 2H), 2.71 (s, 1H), 2.15-2.26 (m, 1H), 2.06-2.15 (m, 2H), 1.98-2.05 (m, 2H), 1.30 (br d, J = 11.28 Hz, 4H) |
| 1.8 | ¹H NMR (400 MHz, DMSO-$d_6$) δ 8.73 (d, J = 1.39 Hz, 1H), 8.02 (dd, J = 1.90, 7.98 Hz, 1H), 7.70 (d, J = 7.98 Hz, 1H), 7.21 (d, J = 8.62 Hz, 2H), 6.98-7.05 (m, 1H), 6.94 (d, J = 2.03 Hz, 1H), 6.88 (d, J = 8.62 Hz, 2H), 6.83-7.10 (t, 1H), 6.77-6.85 (m, 1H), 5.40 (d, J = 4.06 Hz, 2H), 4.81-4.91 (m, 2H), 3.59 (t, J = 5.83 Hz, 2H), 3.51-3.57 (m, 1H), 3.08-3.11 (m, 2H), 3.01-3.06 (m, 2H), 2.54 (s, 3H), 2.03 (s, 3H) |
| 1.9 | ¹H NMR (400 MHz, DMSO-$d_6$) δ 9.43-9.54 (m, 1H), 8.87 (d, J = 1.52 Hz, 2H), 8.17 (dd, J = 1.52, 8.11 Hz, 2H), 7.96 (d, J = 7.86 Hz, 2H), 7.57-7.71 (m, 2H), 7.26 (d, J = 8.74 Hz, 2H), 6.97 (d, J = 8.87 Hz, 2H), 5.46 (s, 3H), 4.86-4.95 (m, 2H), 3.63-3.76 (m, 1H), 3.11-3.21 (m, 2H), 3.04-3.12 (m, 3H), 2.04 (s, 3H) |
| 1.10 | ¹H NMR (400 MHz, DMSO-$d_6$) δ 8.84 (d, J = 1.27 Hz, 1H), 8.13 (dd, J = 1.46, 8.05 Hz, 1H), 7.92 (d, J = 7.98 Hz, 1H), 7.57 (s, 1H), 7.02-7.05 (m, 1H), 7.02 (d, J = 9.51 Hz, 1H), 7.00-7.02 (m, 1H), 6.94-6.99 (m, 1H), 6.93 (s, 1H), 6.89-6.92 (m, 1H), 6.86-6.90 (m, 1H), 6.86-6.91 (m, 1H), 5.48 (s, 2H), 3.49-3.59 (m, 4H), 2.91-3.00 (m, 2H), 2.81-2.91 (m, 2H), 1.21-1.28 (m, 2H), 1.10-1.20 (m, 2H) |
| 1.11 | ¹H NMR (400 MHz, DMSO-$d_6$) δ 8.84 (d, J = 1.39 Hz, 1H), 8.13 (dd, J = 1.46, 8.05 Hz, 1H), 8.03 (d, J = 2.28 Hz, 1H), 7.92 (d, J = 7.98 Hz, 1H), 7.56 (s, 1H), 7.44 (d, J = 2.53 Hz, 1H), 7.42 (d, J = 2.66 Hz, 1H), 7.00-7.04 (m, 1H), 6.91 (d, J = 9.51 Hz, 1H), 6.76 (d, J = 8.74 Hz, 1H), 5.48 (s, 2H), 3.48-3.53 (m, 2H), 3.44-3.48 (m, 2H), 3.34-3.41 (m, 2H), 2.07 (s, 1H), 2.02 (s, 3H), 1.15-1.20 (m, 2H), 1.08-1.12 (m, 2H) |
| 1.12 | ¹H NMR (400 MHz, DMSO-$d_6$) δ 8.87 (s, 1H), 8.17 (dd, J = 1.33, 8.05 Hz, 1H), 7.96 (d, J = 8.11 Hz, 1H), 7.55 (br t, J = 9.00 Hz, 1H), 7.40-7.49 (m, 1H), 6.78 (d, J = 2.15 Hz, 1H), 6.74 (d, J = 2.03 Hz, 1H), 6.71 (d, J = 2.41 Hz, 1H), 6.68 (d, J = 2.41 Hz, 1H), 5.48 (s, 2H), 3.53 (br s, 3H), 3.15-3.22 (m, 3H), 3.07-3.15 (m, 2H), 2.02 (s, 3H), 1.32 (br s, 2H), 1.24 (br s, 2H) |
| 1.13 | ¹H NMR (400 MHz, DMSO-$d_6$) δ 8.84 (d, J = 1.39 Hz, 1H), 8.14 (d, J = 1.39 Hz, 1H), 8.12 (d, J = 1.52 Hz, 1H), 7.92 (s, 1H), 7.90 (s, 1H), 7.55 (s, 1H), 6.99 (d, J = 2.91 Hz, 2H), 6.89 (s, 1H), 6.87 (s, 1H), 6.85-6.90 (m, 1H), 5.47 (s, 2H), 3.50-3.57 (m, 2H), 2.75-2.79 (m, 2H), 2.67-2.72 (m, 2H), 2.20 (s, 3H), 2.02 (s, 3H), 1.18-1.24 (m, 2H), 1.10-1.14 (m, 2H) |

Analytical HPLC Methods

Method A

| time (min) | Vol.-% water (incl. 0.1% NH₄OH) | Vol.-% ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3 |
| 1.40 | 0 | 100 | 3 |

Analytical column: XBridge C18 (Waters) 2.5 µm; 3.0 × 30 mm; column temperature: 60° C.

Method B

| time (min) | Vol.-% water (incl. 0.1% TFA) | Vol.-% ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Stable Bond (Agilent) 1.8 µm; 3.0 × 30 mm; column temperature: 60° C.

Method C

| time (min) | Vol.-% water (incl. 0.1% NH₄OH) | Vol.-% ACN | Flow [mL/min] |
|---|---|---|---|
| 0.00 | 95 | 5 | 1.5 |
| 1.30 | 0 | 100 | 1.5 |
| 1.50 | 0 | 100 | 1.5 |
| 1.60 | 95 | 5 | 1.5 |

Analytical column: XBridge C18_3.0 × 30 mm_2.5 µm (Waters); column temperature: 60° C.

Method D

| time (min) | Vol.-% water (incl. 0.1% TFA) | Vol.-% ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

The invention claimed is:

1. A compound selected from the group consisting of

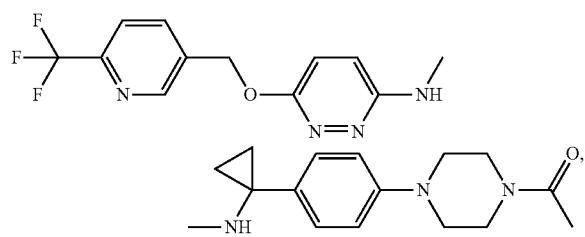

-continued

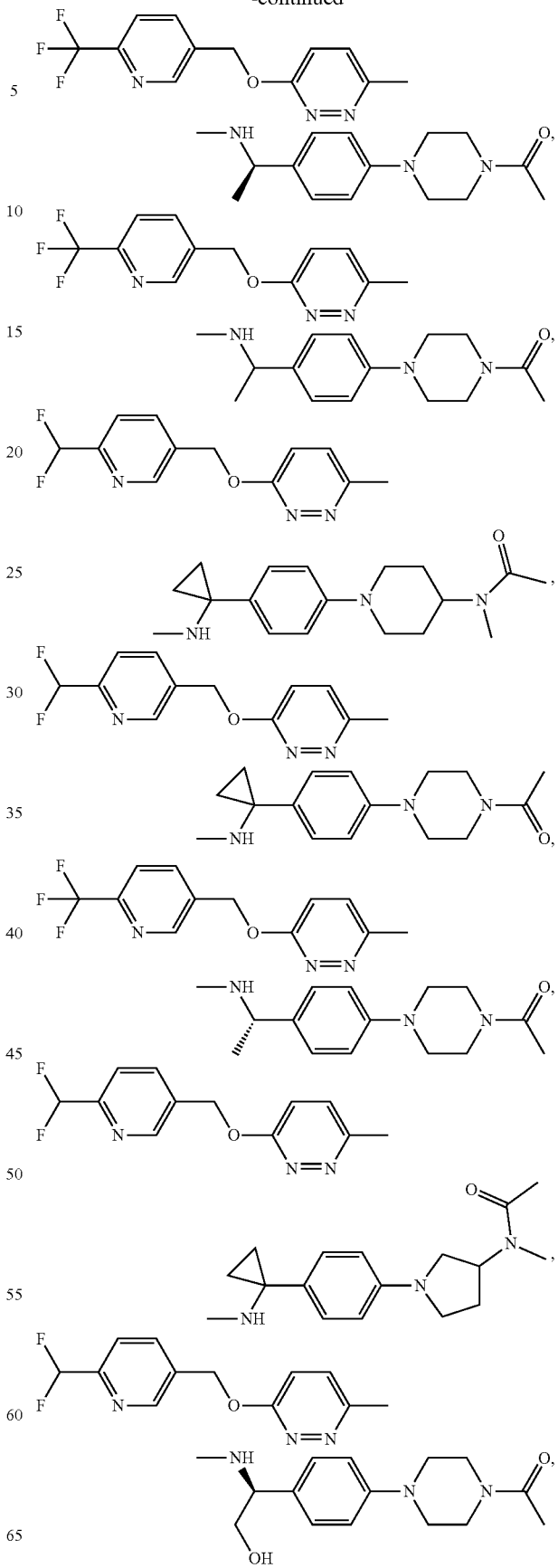

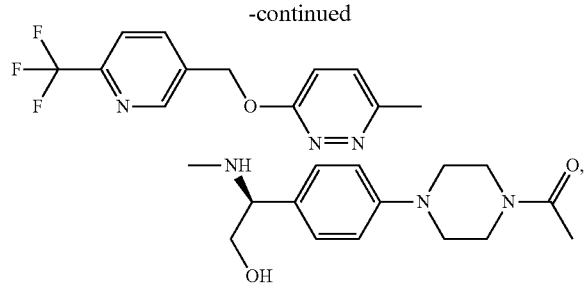
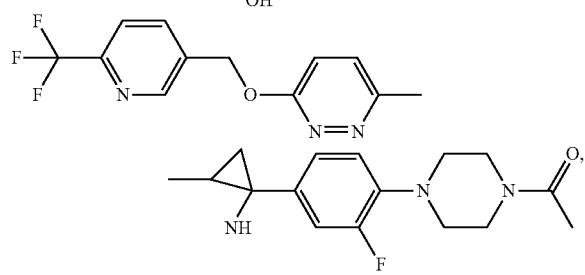
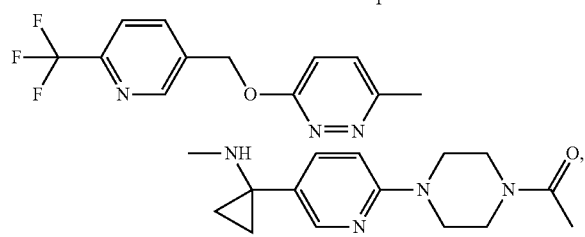
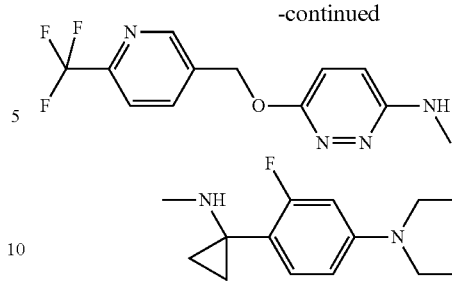
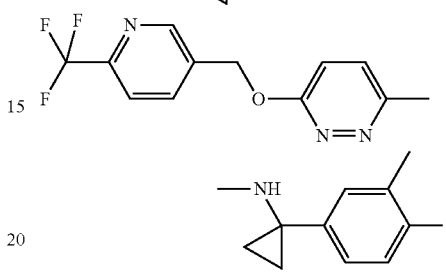
2. A pharmaceutical composition comprising at least one compound according to claim 1 and one or more pharmaceutically acceptable excipients.
3. A method for the treatment of idiopathic pulmonary fibrosis (IPF) or systemic sclerosis (SSc) comprising administering to a human being an effective amount of a compound according to claim 1.
* * * * *